United States Patent [19]

Sinclair

[11] Patent Number: 5,424,346
[45] Date of Patent: Jun. 13, 1995

[54] BIODEGRADABLE REPLACEMENT OF CRYSTAL POLYSTYRENE

[75] Inventor: Richard G. Sinclair, Columbus, Ohio

[73] Assignee: Ecopol, LLC, Golden, Colo.

[21] Appl. No.: 240,085

[22] Filed: May 9, 1994

Related U.S. Application Data

[63] Continuation of Ser. No. 579,465, Sep. 6, 1990, abandoned, which is a continuation-in-part of Ser. No. 387,670, Jul. 31, 1989, abandoned, which is a continuation-in-part of Ser. No. 229,939, Aug. 8, 1988, abandoned.

[51] Int. Cl.$^6$ .............................................. C08L 67/04
[52] U.S. Cl. ..................................... 524/108; 524/311; 524/320; 525/411; 525/415; 525/450
[58] Field of Search .............. 528/354, 361; 525/411, 525/415, 450; 524/108, 311, 320

[56] References Cited

U.S. PATENT DOCUMENTS

| | | |
|---|---|---|
| 1,995,970 | 3/1935 | Dorough . |
| 2,396,994 | 3/1946 | Filachione et al. . |
| 2,438,208 | 3/1948 | Filachione et al. . |
| 2,703,316 | 3/1955 | Schneider . |
| 2,758,987 | 8/1956 | Salzberg . |
| 2,951,828 | 9/1960 | Zeile et al. . |
| 3,268,487 | 4/1966 | Klootwijk . |
| 3,531,561 | 9/1970 | Trehu . |
| 3,565,869 | 2/1971 | DeProspero . |
| 3,636,956 | 1/1972 | Schneider . |
| 3,755,558 | 8/1973 | Scribner ............................ 424/47 |
| 3,773,919 | 11/1973 | Boswell et al. . |
| 4,137,921 | 2/1979 | Okuzumi et al. . |
| 4,279,249 | 7/1981 | Vert et al. . |
| 4,539,981 | 9/1985 | Tunc . |
| 4,603,695 | 8/1986 | Ikada et al. . |
| 4,683,288 | 7/1987 | Tanaka et al. . |
| 4,719,246 | 1/1988 | Murdoch et al. . |
| 4,728,721 | 3/1988 | Yamamoto et al. . |
| 4,789,726 | 12/1988 | Hutchinson . |
| 4,797,468 | 1/1989 | De Vries . |
| 5,076,983 | 12/1991 | Loomis et al. ..................... 264/101 |

FOREIGN PATENT DOCUMENTS

| | | |
|---|---|---|
| 808731 | 3/1969 | Canada . |
| 923245 | 3/1973 | Canada . |
| 0058481 | 8/1982 | European Pat. Off. . |
| 0311065 | 4/1989 | European Pat. Off. . |
| 0314245 | 5/1989 | European Pat. Off. . |
| 0316992 | 5/1989 | European Pat. Off. . |
| 0321176 | 6/1989 | European Pat. Off. . |
| 0368571 | 5/1990 | European Pat. Off. . |
| 14548 | 4/1958 | German Dem. Rep. . |
| 69212 | 10/1969 | German Dem. Rep. . |
| 946664 | 8/1956 | Germany . |
| 1112293 | 8/1961 | Germany . |
| 1153902 | 9/1963 | Germany . |
| 3820299 | 12/1988 | Germany . |
| 41-17675 | 10/1966 | Japan . |
| 61-36321 | 2/1986 | Japan . |
| 1-225622 | 9/1989 | Japan . |
| 99836 | 12/1961 | Netherlands . |
| 755447 | 8/1956 | United Kingdom . |
| 779291 | 7/1957 | United Kingdom . |
| 825335 | 12/1959 | United Kingdom . |
| 932382 | 7/1963 | United Kingdom . |
| 1048088 | 11/1966 | United Kingdom . |
| 1593288 | 7/1981 | United Kingdom . |
| 84/00303 | 2/1984 | WIPO . |
| 9001521 | 2/1990 | WIPO . |

OTHER PUBLICATIONS

Kleine, Von Joyannes et al; An Investigation of the Stereochemistry of Macromolecular Compounds; Report from the Research Laboratory for Macromolecular Chemistry; Makromolekulare Chemie, vol. 30, 1959, pp. 23–38.

Schulz, Rolf C.; Some Optically Active Polyesters and Polyamides; IUPAC International Symposium on Macromolecular Chemistry, Budapest 1969, pp. 185–212.

Fischer, E. W. et al; Investigation of the structure of solution grown crystals of lactide copolymers by means of chemical reactions; Kolloid-Z.u.Z. Polymere 251, 1973, pp. 980–990.

Schindler, A. et al; Biodegradable Polymers for Sustained Drug Delivery; paper given at Key Biscayne, Fla., Nov. 20–24 1976, Contemporary Topics in Polymer Science, ed. by E. M. Pearce and J. R. Schaefgen, Plenum Press, New York, vol. 2, 1977, pp. 251–289.

Vert, Michel et al; Stereoregular Bioresorbable Polyesters for Orthopaedic Surgery; Makromol. Chem., Suppl. 5, 1981, pp. 30–41.

Wehrenberg II, Robert H.; Lactic acid polymers: strong, degradable thermoplastics; Materials Engineering, Sep. 1981, pp. 63–66.

Christel, P. et al; Biodegradable Composites for Internal Fixation; Adv. Biomaterials, 3, 1982, pp. 271–280.

Editorial, Materials Engineering, May 1982, p. 56.

Chabot, Francois et al; Configurational structures of lactic acid stereocopolymers as determined by $^{13}C-[^1H]$ n.m.r.; Polymer, vol. 24, Jan. 1983, pp. 53–59.

Vert, Michel et al; Bioresorbable Plastic Materials for Bone Surgery; Macromolecular Biomaterials, Chapter 6, Editors–Garth W. Hastings and Paul Ducheyne, CRC Press, Inc. Boca Raton, Florida, 1984, pp. 120–142.

Vert, M.; Biomedical Polymers from Chiral Lactides and Functional Lactones: Properties and Applications; Makromol. Chem., Macromol. Symp., 6, 1986, pp. 109–122.

Cohn, D. et al; Amorphous and crystalline morphologies in glycolic acid and lactic acid polymers; Polymer, vol. 28, Nov., 1987, pp. 2018–2022.

Gerlach, K. L., et al; In vivo tests of the stability of biodegradable polymers for use as osteosynthesis materials; Dtsch Z Mund Kiefer Gesichtscher, 11, 1987, pp. 211–216.

Sinclair, R. G.; Lactic Acid Polymers—Controlled Release Applications for Biomedical Use and Pesticide Delivery; Proceedings of the First Annual Corn Utilization Conference, Jun. 11–12, 1987, pp. 221–236.

Gerlach, K. L. et al; Comparative Studies of the Long-Term Vibration Resistence of Absorbable Polymers in Oral (Mouth and Jaw) Surgery; Dtsch. Zahnaerztl. Z., 43, 1988, pp. 376–378.

Bodmeier, R.; The effect of the addition of low molecular weight poly DL-lactide) on drug release from biodegradable poly(DL-lactide) drug delivery systems; International Journal of Pharmaceutics, 51, 1989, pp. 1–8.

Boehringer Ingelheim KG, Chemicals Division, D-6507 Ingelheim W. Germany, Resomer ® Resorbable Polyesters.

Fukuzaki, Hironobu et al; Low-molecular-weight copolymers composed of L-lactic acid and various DL-hydroxy acids as biodegradable carriers; Makromol. Chem. 190, 1989, pp. 2571–2577.

Yui, Nobuhiko et al; Stereo block copolymers of L- and D-lactides; Makromol. Chem., 191, 1990, pp. 481–488.

*Primary Examiner*—Patricia A. Short
*Attorney, Agent, or Firm*—Sheridan Ross & McIntosh

[57] ABSTRACT

The biodegradable polymer comprises polymerized lactic acid units of the structure:

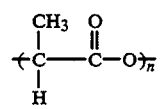

where n is an integer between 450 and 10,000 and the alpha carbon is a mixture of L- and D-configurations with a preponderance of either D- or L-units, wherein the polymer is suitable for replacement of polystyrene; the biodegradable composition also comprises blends of a physical mixture of polymerized lactic acid units of the formula I, where n is an integer between 450 and 10,000 and the alpha carbon is a mixture of L- and D-configurations with a preponderance of either D- or L-units, and a homopolymer of poly(D-lactic acid) or poly(L-lactic acid), and plasticizers that provide unique properties when intimately dispersed.

18 Claims, 9 Drawing Sheets

BIODEGRADABLE REPLACEMENT OF CRYSTAL POLYSTYRENE

This is a continuation of application Ser. No. 07/579,465, entitled "BIODEGRADABLE REPLACEMENT OF CRYSTAL POLYSTYRENE" and filed on Sep. 6, 1990, now abandoned, which is a continuation-in-part of application Ser. No. 07/387,670, entitled "BIODEGRADABLE REPLACEMENT OF CRYSTAL POLYSTYRENE" and filed on Jul. 31, 1989, now abandoned, which is a continuation-in-part of application Ser. No. 07/229,939, entitled "BIODEGRADABLE REPLACEMENT OF CRYSTAL POLYSTYRENE" and filed on Aug. 8, 1988, now abandoned.

FIELD OF THE INVENTION

This invention discloses a material and process of preparing it which is an offset, that is a replacement for crystal polystyrene, sometimes known as orientable polystyrene or OPS. The material is an offset for crystal polystyrene but is composed of a polyester capable of degrading in the environment over approximately one years time. The material is a polyester, comprised of polymerized lactic acid, prepared from either D-lactic acid or L-lactic acid, and D,L-lactic acid. The ratio of the two polymerized monomer units, the process treatment and in some cases certain adjuvants, determine the precise physical properties required for the exacting requirements of a crystal polystyrene offset. Thus, at approximately a ratio of 90/10, L-lactic/D,L-lactic acid, the polymerized lactic acid (PLA) is a well behaved thermoplastic that is clear, colorless, and very stiff. As such it is very suitable for preparing films, foams, and other thermoformed items of disposable or one-way plastic. Having served its purpose as a packaging plastic, the poly(lactic acid) slowly environmentally biodegrades to innocuous products when left in the environment. This harmless disappearance can help alleviate the mounting problems of plastic pollution in the environment.

The present application is related to the application entitled BIODEGRADABLE PACKAGING THERMOPLASTICS FROM POLYLACTIC ACID having Ser. No. 07/579,005, and the application entitled BLENDS OF POLYLACTIC ACID having Ser. No. 579,000, and the application entitled DEGRADABLE IMPACT MODIFIED POLYLACTIC ACID, having Ser. No. 07/579,460, all having the same assignee and filing date as the present application, the disclosures of which are incorporated by reference herein.

BACKGROUND OF THE INVENTION

There is a need for an environmentally biodegradable packaging thermoplastic as an answer to the tremendous amounts of discarded plastic packaging materials. U.S. plastic sales in 1987 were 53.7 billion lbs of which 12.7 billion lbs were listed as plastics in packaging. A significant amount of this plastic is discarded and becomes a plastic pollutant that is a blot on the landscape and a threat to marine life. Mortality estimates range as high as 1-2 million seabirds and 100,000 marine mammals per year.

A further problem with the disposal of plastic packaging is the concern for dwindling landfill space. It has been estimated that most major cities will have used up available landfills for solid waste disposal by the early 1990's. Plastics comprise approximately 3 percent by weight and 6 percent of the volume of solid waste.

One other disadvantage of conventional plastics is that they are ultimately derived from petroleum, which leaves plastics dependent on the uncertainties of foreign crude oil imports. A better feedstock would be one that derives from renewable, domestic resources.

However, there are good reasons for the use of packaging plastics. They provide appealing aesthetic qualities in the form of attractive packages which can be quickly fabricated and filled with specified units of products. The packages maintain cleanliness, storage stability, and other desirable qualities such as transparency for inspection of contents. These packages are known for their low cost of production and chemical stability. This stability, however leads to very long-life of the plastic, so that when its one-time use is completed, discarded packages remain on, and in, the environment for incalculably long times.

It will be appreciated by those skilled in the art that duplicating the properties of one thermoplastic with another is not predictable. Thus, with crystal polystyrene, there are exacting requirements for satisfactory performance of the polystyrene, which has been developed over many years to meet manufacturing and end-use specifications of crystal polystyrene grades.

There are many citations in the prior art for the preparation of lactic acid polymers and copolymers. The earliest processes used lactic acid directly as the monomer, cf., e.g., U.S. Pat. Nos. 1,995,970; 2,362,511; and 2,683,136. The poly(lactic acids) of these patents were of low molecular weights, tacky and without good physical properties. U.S. Pat. No. 2,668,162 (Lowe, DuPont) discloses the use of lactide as the monomer. Lactide is the dilactone of lactic acid and is an internal ester of lactic acid. When lactide is formed, byproduct water is eliminated, permitting the lactide subsequently to be ring-opened polymerized to linear polyester of high molecular weight without tedious condensation methods. Polymers and copolymers of excellent physical properties were obtained by using the intermediate, lactide, to form poly(lactic acid). Copolymers of lactide and glycolide are disclosed by the Lowe patent which are tough, clear, cold-drawable, stretchable, and capable of forming at 210 C. into self-supporting films.

U.S. Pat. No. 2,703,316 discloses lactide polymers which can be a "wrapping tissue" material that is intrinsically stiff and brittle. The lactide monomer is specified as having a melting point greater than 120 C. L-lactide monomer melts at 95 C. and D,L-lactide melts at 128 C.

U.S. Pat. No. 2,758,987 discloses homopolymers of either L- or D,L-lactide which are described as melt-pressable into clear, strong, orientable films. The properties of the poly(L-lactide) are given as: tensile strength, 29,000 psi; percent elongation, 23 percent, tensile modulus 710,000 psi. The poly(D,L-lactide) properties were: 26,000 psi tensile strength; 48 percent elongation; and a tensile modulus of 260,000 psi. Copolymers of L- and D,L-lactide, that is copolymers of L- and D,L-lactic acid, are disclosed only for a 50/50 by weight mixture. Only tack point properties are given (Example 3). It was claimed that one antipodal (optically active, e.g., L-lactide) monomer species is preferred for the development of high strength.

U.S. Pat. No. 2,9510828 discloses a bead polymerization of alpha-hydroxy carboxylic acids such as lactic acid. Copolymers of L- and D,L-lactic are cited at ratios of 75/25, 50/50 and 25/75, respectively. However, no physical properties are given except for particle sizes of the beads and softening points which are all generally in the 110–135 C. range.

U.S. Pat. Nos. 3,297,033; 3,463,158; 3,531,561; 3,636,956; 3,736,646; 3,739,773; and 3,797,499 all disclose lactide polymers and copolymers that are strong crystalline, orientable polymers suitable for fibers and suture materials. These disclosures teach the use of highly-crystalline materials, which are oriented by drawing and annealing to obtain tensile strengths and moduli, typically, greater than 50,000 psi and 1,000,000 psi, respectively. Although formability is mentioned into a variety of shaped articles, physical properties of unoriented extrudates and moldings are not mentioned. For example, U.S. Pat. No. 3,636,956 teaches the preparation of a copolymer having 85/15, 90/10, 92.5/7.5, or a 95/5 weight ratio of L-lactide/D,L-lactide; drawn, oriented fibers are cited; other plasticizers such as glyceryl triacetate, and dibutyl pthalate are tought; however, it is preferred in this disclosure to use pure L-lactide monomer for greater crystallinity and drawn fiber strength; and finally, the advantages of the present invention (e.g. an intimate dispersion of lactic acid based plasticizers that provides unique physical properties) are not obtained.

U.S. Pat. No. 3,797,499 teaches the copolymerization of 95/5 weight ratio, of L-lactide/D,L-lactide (Example V); however, the material is formed into filaments. In column 5, line 1 Schneider teaches against enhanced properties in the range provided in the present invention. Plasticizers such as glyceryl triacetate, ethyl benzoate and diethyl phthalate are used.

Okuzumi et al, U.S. Pat. No. 4,137,921, in Example 4, teaches a 90/10 random copolymer of L-lactide and D,L-lactide, however, the advantages of the present invention are not obtained. Hutchinson, U.S. Pat. No. 4,789,726, teaches a process for the manufacture of polyesters, particularly polylactides of low molecular weight, by forming high molecular weight material and then degrading it to lower weight products of controlled polydispersity, however, monomers are removed in the process.

U.S. Pat. Nos. 3,736,646; 3,773,919; 3,887,699; 4,273,920; 4,471,077; and 4,578,384 teach the use of lactide polymers and copolymers as sustained-drug release matrices that are biodegradable and biocompatible. Again, physical properties of the polymers from ordinary thermoforming methods such as film extrusion or molding are not mentioned.

Other patent art which teach the preparation of L-lactide/D,L-lactide copolymers are Offenlegungsschrift 2,118,127 cites a snow-white, obviously crystalline polymer, no other physical properties were given for this copolymer; Canadian Patent 808,731, Canadian Patent 863,673, and Canadian Patent 923,245. The manufacture of films and fibers from the lactide copolymers is mentioned, but physical property data are limited again to drawn fibers.

Additional related art includes: Low molecular weight poly(D,L-lactide) has been recently added to high molecular weight D,L-lactide along with a drug such as caffeine, salicylic acid, or quinidine, see R. Bodmeier et al, International J. of Pharm. 51, pp. 1–8, (1989). Chabot et al in polymerizing L-lactide and racemic D,L-lactide for medical applications removed residual monomer and lower oligomers, see Polymer, Vol. 24, pp. 53–59, (1983). A. S. Chawla and Chang produced four different molecular weight D,L-lactide polymers but removed monomer for in vivo degradation studies, see Biomat., Med. Dev. Art. Org., 13(3&4), pp. 153–162, (1985-86). Kleine and Kleine produce several low residual monomer, poly(lactic acids) from D,L-lactide while determining lactide levels during the polymerization, see Macromolekulare Chemie, Vol. 30, pp. 23–38, (1959); Kohn et al also makes a low residual monomer product while monitoring the monomer content over time, see Journ. Appl. Polymer Science, Vol. 29, pp. 4265–4277, (1984). M. Vert et al teaches high molecular weight polymers with elimination of residual monomer, see Makromol. Chem., Suppl. 5, pp. 30–41, (1981). M. Vert, in Macromol. Chem., Macromol. Symp. 6, pp.109–122, (1986), discloses similar poly(L-/D,L-lactide) materials, see Table 6, p. 118. In European patent application EP 311,065 (1989) poly(D,L-lactide) is prepared as an implant material for drug delivery during degradation, the material contains drugs, low molecular weight polylactide, and other additives; EP 314,245 (1989) teaches a polylactide having a low amount of residual monomer, the polymer is prepared by polymerization of meso D,L-lactide as a homopolymer or with other lactide monomers, the advantages of the present invention are not obtained; and West German Offenlegungsschrift DE 3,820,299 (1988) teaches the polymerization of meso D,L-lactide with lactides, however, the advantages of the present invention are not obtained.

Of particular interest, U.S. Pat. No. 4,719,246 teaches the blending of homopolymers of L-lactide, D-lactide, polymers or mixtures thereof; and copolymers of L-lactide or D-lactide with at least one nonlactide comonomer. The blending is intended to produce compositions having interacting segments of poly(L-lactide) and poly(D-lactide).

BRIEF DESCRIPTION OF THE INVENTION

In general, a first embodiment of the invention provides for an environmentally decomposable polymeric composition suitable for use as a substitute for crystal polystyrene. The composition comprises a poly(lactic acid), where the repeating unit is an L- or D-enantiomer and there is a preponderance of either enantiomer, having intimately dispersed therein a plasticizer, as described below, wherein the unoriented composition has the physical properties of a tensile strength of at least 5,000 psi, a tangent modulus of at least 200,000 psi, and is colorless. The composition can be adjusted to be form stable above about 70 C.

A second embodiment of the invention provides for a substitute for crystal polystyrene comprising a copolymer of the formula:

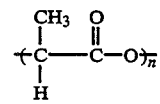

I where n is an integer between about 450 and about 10,000, where the repeating unit is an L-or D-enantiomer and there is a preponderance of either enantiomer; and having intimately dispersed therein between about 0.1 and about 10 weight percent of a plasticizer, as described below, wherein the unoriented composition has the physical properties of a tensile strength of at least about 5,000 psi, a tangent modulus of at least about 200,000 psi, and form stability above about 70 C., and is colorless. The ratio of L-enantiomer to D-enantiomer is preferably between about 99/1 and about 1/99 and most preferably between about 2.5/97.5 and 7.5/92.5, or between about 92.5/7.5 and 97.5/2.5.

A third embodiment of the invention provides a composition comprising a physical mixture of (a) a first poly(lactic acid) having a preponderance of either D- or L- enantiomers; (b) a second poly(lactic acid) selected from the group consisting of poly(D-lactic acid) or a poly(L-lactic acid), wherein the weight percent ratio of the first poly(lactic acid) to the second poly(lactic acid) is between about 1/99 and 99/1; and (c) greater than about 0.1 weight perecent of plasticizer as described below, wherein the plasticizer is intimately dispersed within the poly(lactic acid); and the unoriented composition has a tensile strength of at least 5,000 psi and a tangent modulus of at least 200,000 psi, is form stable above 70 C., and is substantially colorless. Prefered ratios of the first and second polylacic acids are between about 98/2 to about 75/25, and most preferably between about 85/15 and about 95/5. The first poly(lactic acid) may be defined by formula I, where n is an integer between about 450 and about 10,000; and the second poly(lactic acid) by the formula:

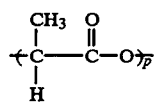

II where p is an integer between about 450 and about 10,000; and the unoriented composition has the physical properties of a tensile strength of at least 5,000 psi and a tangent modulus of at least 200,000 psi, and is colorless.

The composition of the third embodiment may be oriented and annealed to provide a product having a plasticizer intimately dispersed within the poly(lactic acid) and the product has the physical properties of: a tensile strength in excess of 7,500 psi, a tangent modulus in excess of 350,000 psi, and dimensional heat stability at temperatures above 70 C. The product can be biaxially oriented.

A fourth embodiment of the invention provides for an oriented and annealed environmentally decomposable film or sheet product suitable for use as a substitute for oriented crystal polystyrene film or sheet comprising: a film or sheet of a copolymer of the formula I: where n is between about 450 and about 10,000 where the repeating unit is an L-or D-enantiomer and there is a preponderance of either enantiomer; the product having intimately dispersed therein the residue of a plasticizer, as described below; the oriented and annealed product having the physical properties of: a tensile strength in excess of 7,500, a tangent modulus in excess of 350,000, and dimensional heat stability at temperatures above about 70 C. The product may be biaxially oriented. Other embodiments of the product may contain the other plasticizers discussed below.

A fifth embodiment provides for an oriented and annealed environmentally decomposable film or sheet product suitable for use as a substitute for oriented crystal polystyrene film or sheet comprising: a physical mixture of between about 0.09 and about 99 weight percent of a poly(lactic acid) of the formula I: where n is an integer between about 450 and about 10,000 and having a preponderance of either the D- or the L-enantiomers; between about 99 and about 0.09 weight percent of a poly(lactic acid) of the formula IX: where p is an integer between about 450 and about 10,000, and the repeating unit is a D- or an L-enantiomer; below a plasticizer, as described below, intimately dispersed within the poly(lactic acid); and the product has the physical properties of: a tensile strength in excess of 7,500 psi a tangent modulus in excess of 350,000 psi, and is dimensionally heat stable at temperatures above 70 C. The product may be biaxially oriented.

A sixth embodiment provides for an environmentally decomposable polymeric foam composition comprising a copolymer of the formula I: where n is an integer between about 450 and about 10,000, where the repeating unit is an L-or D-enantiomer and there is a preponderance of either enantiomer; having intimately dispersed therein a plasticizer discussed below and wherein the composition is form stable above 70 C.

A seventh embodiment of the invention provides for an environmentally decomposable polylactide product suitable as a substitute for crystal polystyrene comprising: a poly(lactic acid); and a plasticizer, as discussed below, intimately dispersed in the poly(lactic acid), wherein the poly(lactic acid) has a number average molecular weight, Mn, between about 50,000 and 400,000, a tensile strength of at least about 7500 psi and a tangent modulus of at least 350,000, form stability above 70 C., and is substantially clear and colorless after processing into a product.

Plasticizers contemplated for the compositions and processes in the present invention include:
(a) lactic acid, D-lactide, L-lactide, meso D,L-lactide, racemic D,L-lactide, oligomers of lactic acid, oligomers of lactide, and mixtures thereof; where oligomers of lactic acid and oligomers of lactide defined by the formula:

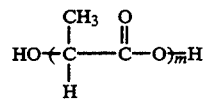

III and where m is an integer: $2 \leq m \leq 75$; and
(b) one or more derivatives of an oligomer of lactic acid defined by the formula:

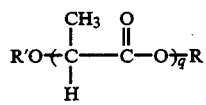

IV where R=H, alkyl, aryl, alkylaryl or acetyl, and R is saturated, where R'=H, alkyl, aryl, alkylaryl or acetyl, and R' is saturated, where R and R' cannot both be H, and where q is an integer: $2 \leq q \leq 75$.

The plasticizers may be present as residual plasticizers from the polymerization reaction, or additional plasticizer that is added to the composition.

To obtain special compositions or processing characteristics the plasticizers may be present as (a) a first plasticizer selected from the group consisting of an oligomer of lactide, or an oligomer of lactic acid; and a second plasticizer selected from the group consisting of lactic acid, D-lactide, L-lactide, meso D,L-lactide, racemic D,L-lactide, and mixtures thereof; and (b) a first plasticizer selected from the group consisting of one or more derivatives of an oligomer of lactic acid defined by the formula IV: where R=H, alkyl, aryl, alkylaryl or acetyl, and R is saturated, where R'=H, alkyl, aryl, alkylaryl or acetyl, and R' is saturated, where R and R' cannot both be H, and where q is an integer: $2 \leq q \leq 75$; and a second plasticizer selected from the group consisting of lactic acid, D-lactide, L-lactide, meso D,L-lactide, racemic D,L-lactide, and mixtures thereof.

The amount of plasticizer present must be above about 0.1 weight percent. The upper limit is defined by the amount of plasticizer that will give the physical properties for crystal polystyrene as defined herein. A preferred amount of plasticizer is between about 0.1 weight percent and about 10 weight percent. The plasticizer may be added for example in an amount (1) effective to provide substantial transparency, (2) effective to prevent degradation during processing, and (3) effective to prevent discoloration during processing. The plasticizer may be added by methods known in the art for blending (e.g. mill blending) to obtain an intimate dispersion.

An eighth embodiment provides for a process for the manufacture of an environmentally decomposable film or sheet forming polymeric composition comprising: copolymerizing a molten blend of monomer selected from the group consisting of D-Lactide, L-lactide, D,L-lactide, meso D,L-lactide, racemic D,L-lactide, and mixtures thereof, wherein the monomers are selected to provide D- and L-enantiomers with a preponderance of either the D-, or L-enantiomers terminating the polymerization reaction prior to completion to provide in the composition an intimately dispersed plasticizer as discussed herein, the unoriented composition having a tensile strength of at least 5,000 psi and a tangent modulus of at least 200,000 psi; and treating the composition to maintain the plasticizer as an intimate dispersion within the polymer whereby a substantially colorless composition is obtained. If desired additional plasticizer may be added after the poymerization reaction is terminated. The composition may also be rendered transparent as described below.

The process preferably selects the the type and amount of monomer to provide a ratio of L-enantiomer to D-enantiomer of between about 1/99 and 99/1. More preferably, the monomer is selected obtain a ratio of L-enantiomer to D-enantiomer of between about 2.5/97.5 and 7.5/92.5 or between about 92.5/7.5 and 97.5/2.5. The process most preferably uses the selected monomers in the molten blend comprising between about 85 and 95 weight percent D-lactide or L-lactide, and between about 5 and 15 weight percent meso D,L-lactide or racemic D,L-lactide.

The polymeric composition may advantageously be extruded into a film or sheet and physically treated by orientation and/or annealing to provide a polymeric film or sheet having a tensile strength of at least 7,500 psi and a tangent modulus of at least 350,000 psi. An additional treatment comprises biaxially orienting and heat treating the polymeric composition.

The treatment may comprise adding nucleating agents, adding D-lactide or L-lactide homopolymer by blending, and orienting the polymer. Color bodies can be excluded by performing the polymerization in an inert atmosphere and at reaction temperatures below 140 C. If desired the treatment step comprises annealing the composition above its glass transition temperature, whereby a higher heat deflection temperature is obtained.

DETAILED DESCRIPTION OF THE INVENTION AND PREFERRED EMBODIMENTS

Figure 1:
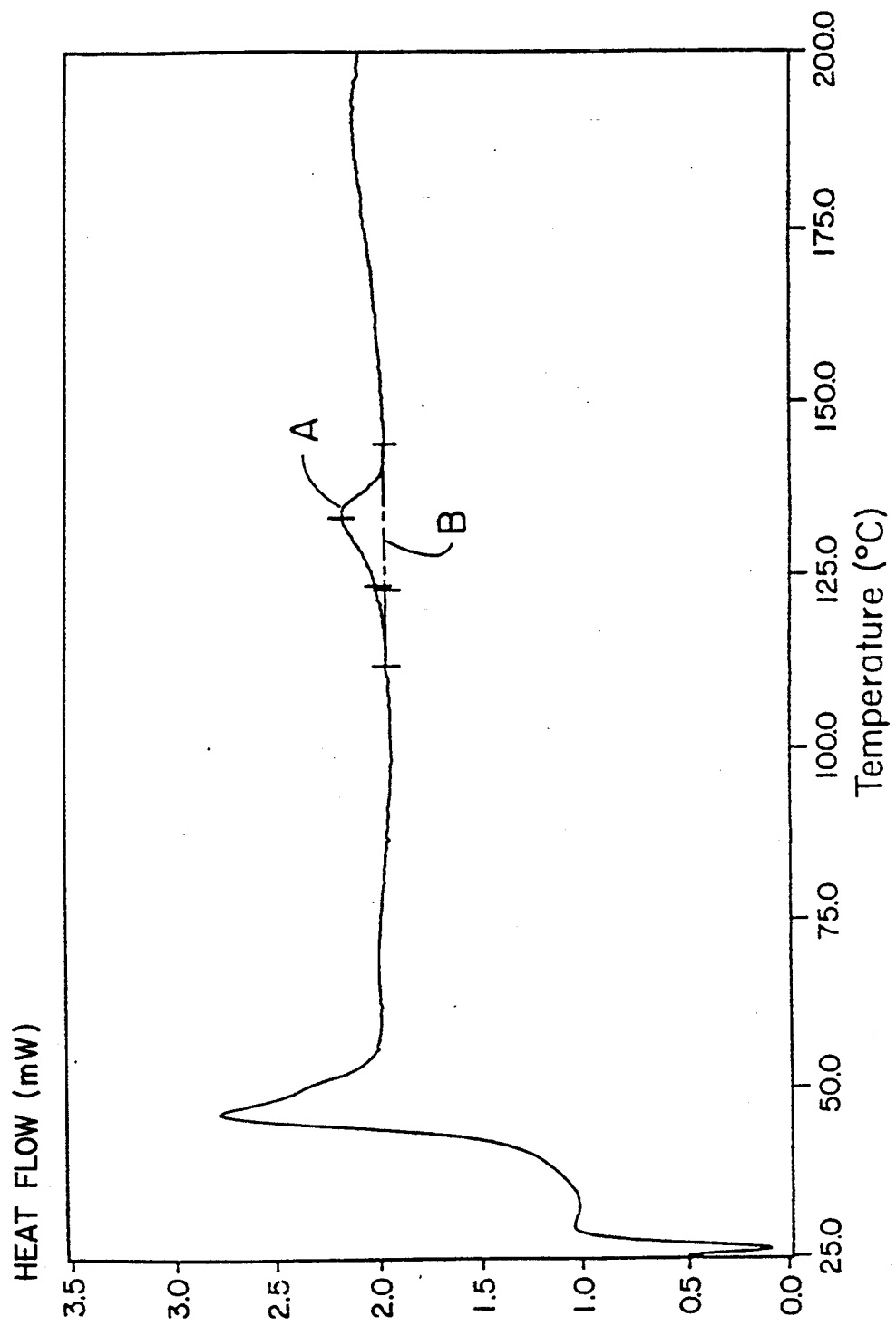
FIG. 1 illustrates the differential scanning calorimetry (DSC) plot of unannealed 90/10, L-/D,L-lactide copolymer of Example 5. A is unquenched while B is quenched.
Figure 2:
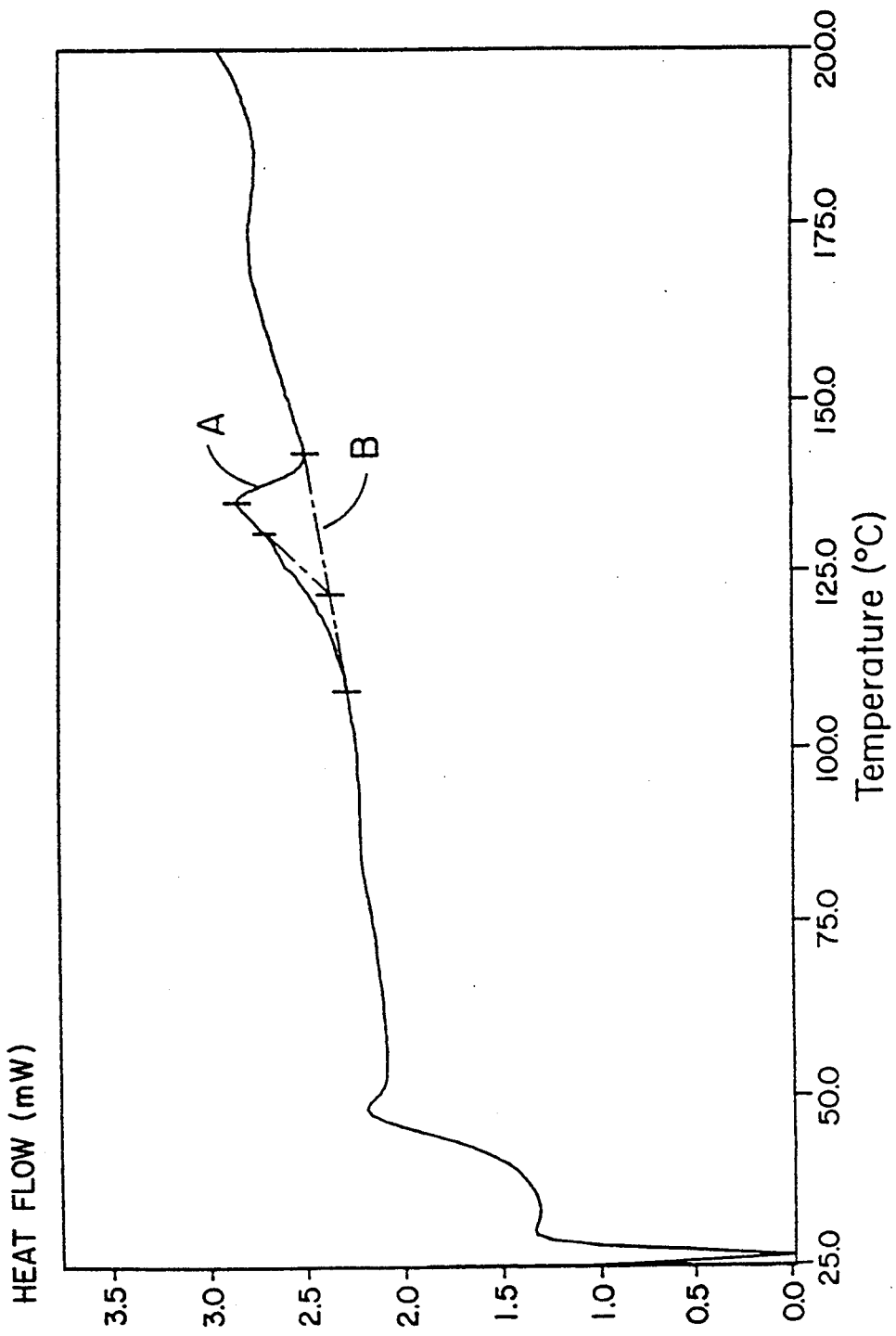
FIG. 2 illustrates the DSC plot of the material of Example 5 after remaining at 70 C. for 100 minutes. A is unquenched while B is quenched.
Figure 3:
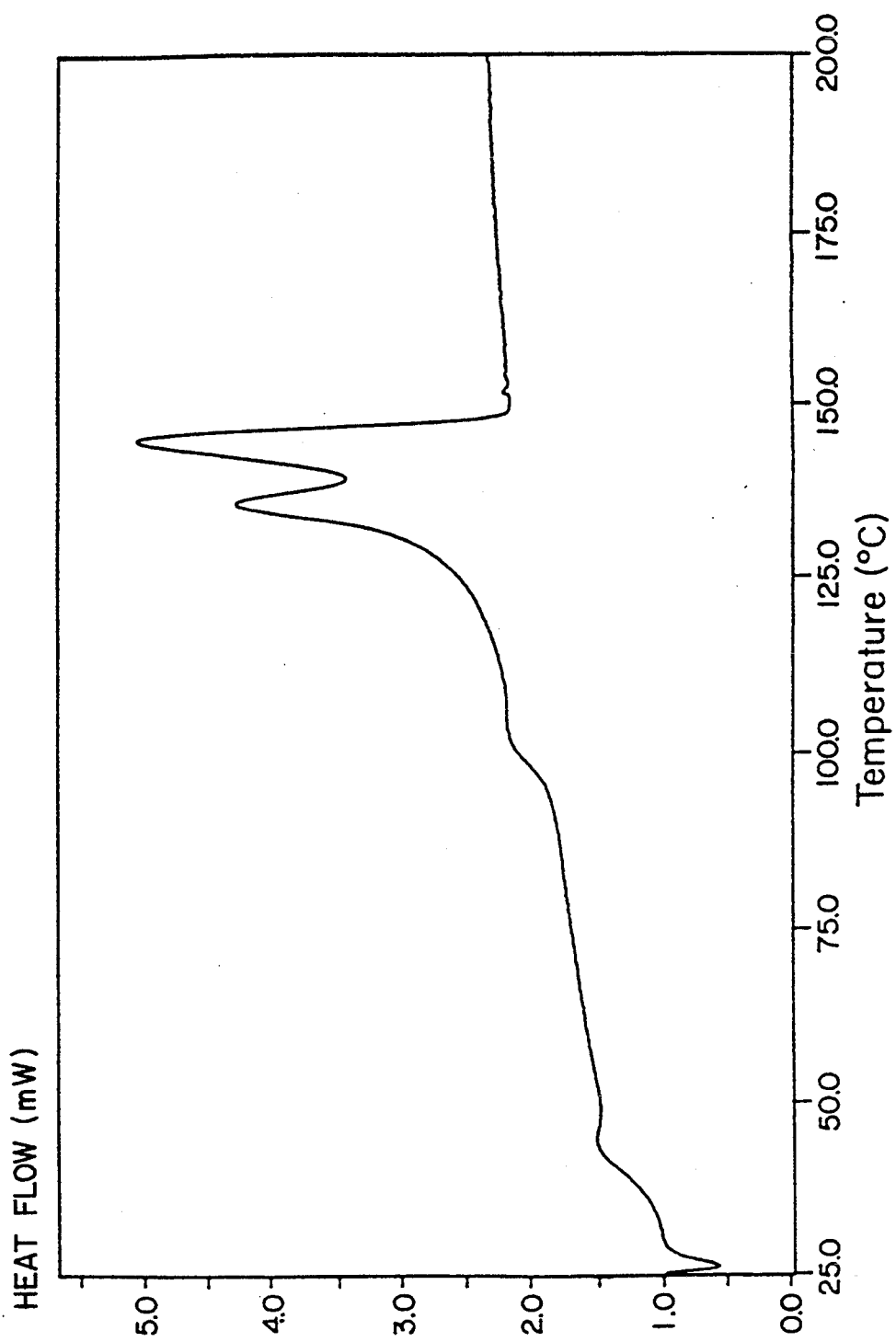
FIG. 3 illustrates the DSC plot of the unquenched material of Example 5 after annealing in 185 F. overnight.
Figure 4:
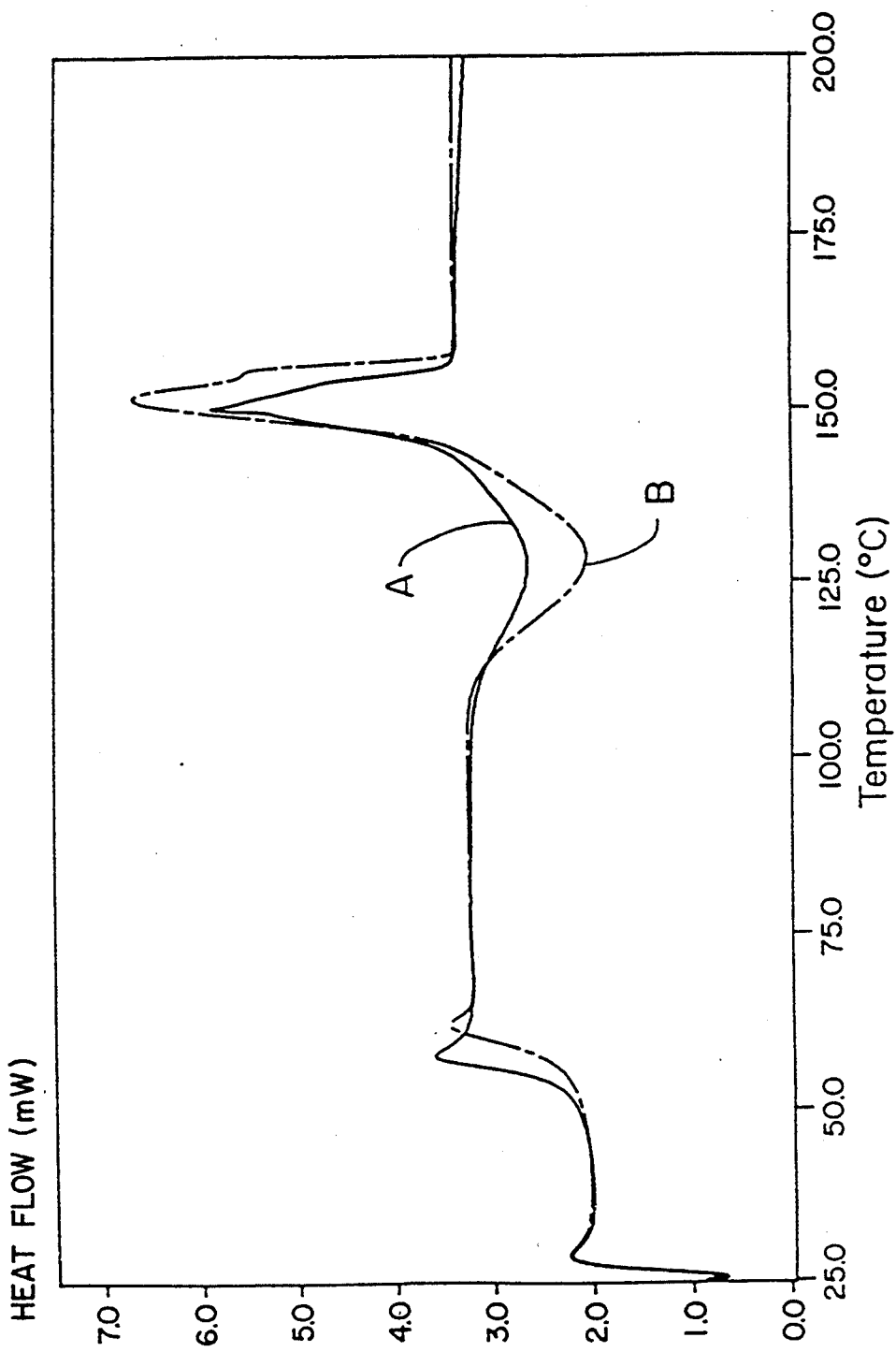
FIG. 4 illustrates the DSC plot of the material of Example 5 that has been blended with 5 percent calcium lactate. A is unquenched while B is quenched.

The environmentally compositions disclosed herein are completely degradable to environmentally acceptable and compatible materials. The intermediate products of the degradation: lactic acid is a widely distributed naturally occurring substance that is easily metabolized by a wide variety of organisms. Its natural end degradation products are carbon dioxide and water. Contemplated equivalents of these compositions such as those that contain minor amounts of other materials, fillers, or extenders can also be completely environmentally degradable by proper choice of materials. The compositions herein provide environmentally acceptable materials because their physical deterioration and degradation is much more rapid and complete than the conventional nondegradable plastics that they replace. Further, since all or a major portion of the composition will be poly(lactic acid), and/or a lactic acid derived lactide or oligomer, no residue or only a small portion of more slowly degrading residue will remain. This residue will have a higher surface area than the bulk product and an expected faster degradation rate. Since both lactic acid and lactide can achieve the same repeating unit, the general term poly(lactic acid) as used herein refers to polymers having the repeating unit of formula I without any limitation as to how the polymer was made (e.g. from lactides, lactic acid, or oligomers), and without reference to the degree of polymerization or level of plasticization.

The preferred composition of the present invention comprises polymerized lactic acid units with the repeating unit:

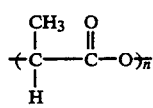

wherein n is an integer with a value between about 450 and about 10,000 and the alpha carbon is a random mixture of D and L (or R and S) with a preponderance of one of the pure enantiomers when plasticized by lactic acid, lactide monomers, oligomers of lactide, oligomers of lactic acid, derivatives of oligomeric lactide and various mixtures thereof. A plasticizer may be produced by stopping the reaction before polymerization is completed. Optionally additional plasticizer consisting of lactide monomers (D-lactide, L-lactide, D,L-lactide, or mixtures thereof), lactic acid, oligomers lactide or oligomers of lactic acid or its derivatives including all L-, D-, and DL- configurations, and mixtures thereof can be added to the formed polymer. The more intimately the plasticizer is integrated within the polymer the better are its characteristics. In fact very intimate dispersion and integration is needed to obtain the advantages of the invention as further discussed below. If desired, additional monomer or oligomer plasticizer can be added to any residual monomer or oligomer remaining in the composition after polymerization. The oligomers of lactic acid and oligomers of lactide defined by the formula:

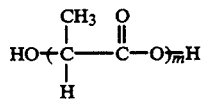

and where m is an integer: $2 \leq m \leq 75$ (including all L-, D-, DL-configurations and mixtures thereof, both random and block configurations, useful for a plasticizer). The derivatives of oligomeric lactic acid (including all L-, D-, DL- configurations and mixtures thereof, both random and block configurations, useful for a plasticizer) are defined by the formula IV:

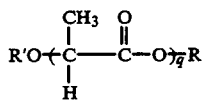

where R=H, alkyl, aryl, alkylaryl or acetyl, and R is saturated, where R'=H, alkyl, aryl, alkylaryl or acetyl, and R' is saturated, where R and R' cannot both be H, and where q is an integer: $2 \leq q \leq 75$, however, the preferable range is: $2 \leq m \leq 10$. The plasticizers added to the polymer compositions have the following functions:

(a) They act as plasticizers introducing pliability and flexibility into the polymer compositions not found in polymer-only composition.

(b) Addition of these plasticizers to the poly(lactic acid) reduces the melt viscosity of the polymers and lowers the temperature, pressure, and shear rate required to melt form the compositions.

(c) The plasticizers prevent heat build up and consequent discoloration and molecular weight decrease during extrusion forming of poly(lactic acid).

(d) The plasticizers add impact resistance to the compositions not found in the polymer alone.

In addition, the plasticizers may act as compatibilizers for melt-blends of polylactides and other degradable and nondegradable polymers. That is, molten mixtures of two different polymers can more intimately associate and mix into well dispersed blends in the presence of the plasticizers. The plasticizers may also improve performance in solution blending.

The subscripts n, m, p, and q above refer to the average number of mers (the repeating unit) of the polymer or oligomer. Number average molecular weight $M_n$ as used below is related to the mers by multiplying n, m, p, or q by the molecular weight of the individual mer, for poly(lactic acid) this number is 72. The number of mers present in a polymer is also called the degree of polymerization. The reader is referred to the following texts where this subject is discussed further: *Polymer Chemistry an Introduction,* 2nd Edition, R. Seymour et al, Marcel Dekker, Inc., 1988 and *Introduction to Polymer Chemistry,* R. Seymour, McGraw-Hill, New York, 1971.

When n is low, the poly(lactic acid), is easily processible, but is considerably weaker than when n is larger. When n is quite large, e.g., 7000 or greater, the poly(lactic acid) is quite strong but difficult to injection mold. Preferably n is approximately 500 to 3000 for the best balance of melt-processibility and end-use physical properties. The amount and type of monomer is selected to obtain L-/D ratios from lactic acid or their cyclic dimer, lactide, as further discussed below. Both lactic acid and lactide achieve the repeating poly(lactic acid) unit, shown above, but lactide is preferred since it more easily obtains the higher molecular weights necessary for good physical properties. Since lactide has two alpha carbons which are assymetric, there are three types of lactide, viz., D,D- (or D-); L, L- (or L-); and meso D,L-lactide.

D-lactide is a dilactide, or cyclic dimer, of D-lactic acid. Similarly, L-lactide is a cyclic dimer of L-lactic acid. Meso D,L-lactide is a cyclic dimer of D- and L-lactic acid. Racemic D,L-lactide comprises a 50/50 mixture of D-, and L-lactide. When used alone herein, the term "D,L-lactide" is intended to include meso D,L-lactide or racemic D,L lactide. The term intimately dispersed as used herein means the material is homogeneously and intimately mixed with the polymer.

Pure poly(L-lactic acid) and poly(D-lactic acid) have poor processing characteristics, easily craze and become opaque. Pure poly(D,L-lactic acid) processes easily but is not as rigid or orientable as the lactide copolymers with a preponderance of D or L configurations. The comonomer ratio of between 85/15 to 95/5 (ratio of L-enantiomer to D-enantiomer would be about 92.5/7.5 to about 97.5/2.5), and most preferably about 90/10, L-lactide/D,L-lactide is a preferred embodiment of the invention. At higher ratios than 95/5, the copolymer is difficult to thermoform without crazing and easily becomes opaque at room temperature. Also, at ratios above 95/5 the material becomes bimorphic and difficult to extrude because of different crystalline forms that affect the processing conditions. Further, above ratios of 95/5 the material must be processed too close to its decomposition point to obtain reasonable viscosities without color formation. At lower ratios than 85/15, the lactide copolymers exhibit lower moduli than the predominantly L or D copolymers. Further, at ratios below 85/15 it is difficult to obtain a required crystallinity in a reasonable time period. In between these limits the copolymers are quenched from the melt in typical manufacturing/processing equipment of plastics technology to achieve films and moldings which are clear, colorless, and extremely rigid. Their properties as formed, above, are closely matched to those properties of a crystal polystyrene. However, a wider range of L-/D-enantiomeric ratio may be useful for special applications.

Another advantage of this invention is that the all-lactic acid copolymer can utilize inexpensive feedstocks. Corn syrup via starch and corn can be fermented to either L- or racemic D,L-lactic acid, depending on the microorganism. Racemic D,L-lactic acid is cheaply obtainable via ethylene which can be oxidized to acetaldehyde, which is reacted with hydrogen cyanide to form lactonitrile, which is hydrolyzed to racemic D,L-lactic acid. Lactide is simply obtained by distillation of lactic acid. No change of the stereochemistry of the asymmetric carbon occurs in transforming lactic acid to lactide by ordinary distillation/condensation methods.

While the reaction of L-lactide and D,L-lactide is discussed herein, it is to be understood that the reactions specifying L-lactide may also use D-lactide. Thus the reaction of D-lactide and D,L-lactide according to the method described herein will give an equivalent product; the only difference being that it rotates light in a different direction.

The copolymers of the present invention are preferably formed by heating the mixture of monomers to form a homogeneous melt and adding a catalyst to cause the lactides to undergo a ring-opening polymerization. The polymerization is preferably carried out in an inert, anhydrous, atmosphere, such as nitrogen or argon, or in a vacuum. Suitable catalysts include divalent metal oxides and organo-metallic compounds such as stannous octoate, zinc acetate, cadmium acetate, aluminum acetate or butanoate, tin chloride, tin benzoate, and antimony oxide. Stannous octoate is the preferred catalyst because of its high solubility in the monomers, ease of preparation in anhydrous form, and low toxicity. The amount of catalyst required can vary from approximately 0.02 to 2 percent by weight, based on monomers and is preferably about 0.2 percent. The molecular weight and melt viscosities of the copolymers are controllable by the amount of catalyst and/or chain-transfer agents such as glycolic acid. The reaction temperature of the polymerization is between approximately 100 to 200 C. The least color formation occurs below 140 C. and the rate of polymerization is best above 135 C. Since racemic D,L-lactide melts at 127 C. it is best for conversion of monomer to polymer to polymerize at a temperature above 127 C.

Where a substantially clear and transparent composition is required, as with crystal polystyrene offsets, the copolymers of this invention are polymerized in an inert atmosphere above their melting points, which are generally in the 125 to 150 C. range. The molten lactide copolymer can be extruded from the polymerizer in strands and rods, quenched, pelletized and stored in bags for use in subsequent molding and extrusion operations.

Similarly, clarity of thermoformed packaging films and shaped articles is achieved by molding and extruding above the copolymer's melting points and fast cooling the fabricated item. Thereafter, the copolymers remain transparent unless heated for several hours above their glass transition temperature, Tg, and below the melting point, Tm. Slow cooling of thermoformed sheets, slabs, films, and molded items can induce spherulite crystallinity in the copolymers which gains improvement in the heat stability of the fabricated item, but causes some loss of transparency. Nucleating agents such as sodium benzoate, calcium lactate, and the like, can also induce rapid and substantial crystallinity. A modest amount of drawing of the copolymer, between its Tg and Tm, induces orientation of the polymer molecules and can substantially improve physical properties without loss of transparency.

Blending of different types of lactide polymer or copolymer can substantially change the physical properties. As an example, the melt-blending of the high-melting L-lactide polymer with a lower melting lactide copolymer can provide a transparent material which has a sufficient amount and type of crystallinity to remain substantially transparent. Those skilled in the art will recognize that transparency in molded films, great stiffness, elevated heat distortion temperature, thermo-processibility, and environmental biodegradability are a rare combination of properties. Thus, the polymers can be blended, as well as nucleated, oriented, and controlled by molecular weight to provide a great deal of latitude in the processibility and final properties in the final compounded thermoplastic.

The copolymers of the present invention will hydrolyze back to lactic acid in the presence of moisture. In the presence of ambient air and humidity the hydrolysis becomes evident in about 12 to 18 months time. The copolymers then become sticky, somewhat opaque, and very brittle. When immersed in water the copolymers show obvious hydrolysis effects in 1 to 4 months time, depending on the composition, molecular weights, the ambient temperature, their surface-to-volume ratio, and the particular, aqueous environment the copolymers are placed in. Microorganisms can further reduce the lactic acid to carbon dioxide and water. As an approximate measure, the copolymers have a shelf life of several months, but disappear within about a year when thoroughly wet.

The following examples are merely illustrative of the present invention. In Examples 1 to 7, a composition series was prepared and evaluated. It was discovered, in contrast to the prior art, that there are distinct differences in the processing behavior and physical properties of the L-lactide/D,L-lactide copolymers.

EXAMPLE 1

In a dry, 500 ml, round-bottom flask was charged 160 g of L-lactide (Purac, Inc., "triple-star" grade) and 40 g of racemic D,L-lactide (Purac, Inc., "triple star" grade). This mixture was heated for approximately 1 hour at 123–129 C. under a stopper with a continuous nitrogen purge through a stopper inlet and outlet. The monomers form a clear melt, which is mixed thoroughly by swirling the melt. Catalyst solution was prepared and dried by azeotropic distillation, that is, 10 ml of stannous octoate (Polysciences, Inc.) was dissolved in 60 ml of toluene; 10 ml of toluene, with trace water, was distilled to a Dean-Stark trap that was vented via a drying tube. A 0.20 ml quantity of the stannous octoate solution was pipetted into the melt and mixed thoroughly. The nitrogen sweep continues and the melt becomes increasingly viscous over the next 3 hours. Heating continues at 123–127 C. for 20–24 hours. The mixture was allowed to cool to room temperature and the flask cooled further with liquid nitrogen behind a shield. The glass shatters and is removed from the polymer by tapping. The copolymer is clear and colorless and is evaluated in a series of tests shown in Table 1. Films were compression molded at 170 C. in a heated hydraulic press for later tensile testing. Slabs, ⅛ inch thick were molded for impact testing by notched Izod, ASTM, D256 and heat deflection temperature, ASTM, D648. Glass transition temperature (Tg) and melting point (Tm, center of the endotherm) were evaluated by differential scanning calorimetry (DSC).

EXAMPLES 2-7

The procedures of Example 1 were repeated except that the ratio of L- and racemic D,L-lactide were changed as shown in Table 1 with the test results. The pure L-lactide polymer, Example 7, would not always mold well at 170-200 C. since it frequently crazed badly on cooling in the mold. Frequently, on cooling, it opacified. FIGS. 1-4 illustrate DSC plots from material of Example 5 as further discussed below.

TABLE 1
PROPERTIES OF L-LACTIDE/RACEMIC D,L-LACTIDE COPOLYMERS

| | Composition, Weight Ratio, L-Lactide/D,L-Lactide (Racemic) | | | | | | |
|---|---|---|---|---|---|---|---|
| | 80/20 | 85/15 | 87.5/12.5 | 90/10 | 90/10 | 95/5 | 100/0 |
| | | | | Example No. | | | |
| | 1 | 2 | 3 | 4 | 5 | 6 | 7 |
| Color/Transparency | colorless & transparent | → | → | → | → | → | white, opaque |
| Film Thickness, mil | 10 | 5 | 15 | 11 | 5 | 10 | 5 |
| Tensile Strength, 1000 psi, ASTM D882 | 7.9 | 6.9 | 8.3 | 8.6 | 8.2 | 9.2 | (a) |
| Elongation, % | 3.5 | 5.8 | 6.0 | 7.1 | 7.2 | 5.1 | (a) |
| Tangent modulus, 1000 psi | 289 | 221 | 694 | 210 | 268 | 748 | — |
| Izod impact strength(b), ft-lb/in. | — | 0.44 | 0.34 | 0.31 | — | 0.41 | (a) |
| $M_w$, 1000's | — | 928 | — | — | — | — | — |
| $M_n$, 1000's | — | 218 | — | — | — | — | — |
| $T_g$, C(c) | 53 | 53 | 48 | 44 | — | 46 | — |
| $T_m$, C(c) | — | — | 125 | 133 | — | 152 | 190 |

(a)Crazes on cooling, too brittle to test.
(b)Notched samples, impacted on notched side on ⅛ in. thick specimens.
(c)Differential scanning calorimetry in nitrogen with 10 C/min. heating rate.

14 hours 125-147 C., then 2 hours 147-131 C. The results are shown in Table 2.

TABLE 2
TENSILE AND MODULUS PROPERTIES OF L-LACTIDE AND D,L-LACTIDE COPOLYMERS

| | Composition, weight Ratio, L-Lactide/D,L-Lactide (Racemic) | | | |
|---|---|---|---|---|
| | 70/30 | 60/40 | 20/80 | 0/100 |
| | | Example No. | | |
| | 9 | 10 | 11 | 12 |
| Color/transparency | Colorless/clear | — | — | — |
| Film thickness, mil | 6-9 | 4-6 | 4-5 | 5-7 |
| Tensile strength,(a) 1000 psi, ASTM D638(a) | 6.9 | 6.7 | 5.8 | 5.6 |
| Elongation, % | 3.2 | 3.0 | 2.7 | 2.8 |
| Tangent modulus, 1000 psi | 287 | 293 | 275 | 278 |

(a)Films were pulled at a jaw separation of 0.2"/min. and chart speed of 5"/min.

The results of the above examples reveal that only certain compositions have the required properties for a crystal polystyrene offset. The main requirements for a crystal polystyrene-like material are clarity and colorlessness, tensile strength greater than 7000 psi, tangent modulus (a measure of stiffness) greater than 400,000 psi and well-behaved thermoplasticity. Table 3 lists some side-by-side comparisons of a crystal polystyrene (OPS) and a 87.5 weight percent L-lactide and 12.5 weight percent racemic D,L-lactide random copolymer.

TABLE 3
PHYSICAL PROPERTY COMPARISONS

| Property | Poly(lactic acid), Example 3 | Crystal Polystyrene |
|---|---|---|
| Impact strength, notched Izod, ft-lb/in. | 0.4 | 0.4 |
| Ultimate tensile strength, psi | 8300 | 7400 |
| Elongation, % | 6.0 | 4.0 |
| Elastic modulus, psi | 694,000 | 450,000 |
| Deflection temperature, F. under load, 264 psi | (a) | 200 |
| Specific gravity | 1.25 | 1.05 |
| Rockwell hardness | (b) | M75 |
| Vicat softening point, F. | (c) | 225 |
| Melt flow rate, D1238(G) | 40–46(d) | 1.7 g/10 min.(e) |

EXAMPLE 8

Similar to Examples 4 and 5, a 90/10 weight ratio copolymer of L-lactide/racemic D,L-lactide was prepared. Into a dry, nitrogen-swept, 2-liter flask was placed 1045.8 g L-lactide and 116.4 g of racemic D,L-lactide. A 1.0 ml quantity of anhydrous stannous octoate (0.2 ml per ml of toluene) solution was added. The flask was swept with nitrogen overnight, then heated in a 141 C. oil bath until the monomers are melted and well mixed, and the heating decreased slowly to 125 C. and continued for 72 hours. The polymer slowly whitens on cooling. After removing the glass, the cloudy, colorless, glassy copolymer was evaluated. Gel permeation chromatography obtains a weight-average molecular weight ($M_w$) of 522,000, and a number-average molecular weight ($M_n$) of 149,000.

Figure 6:
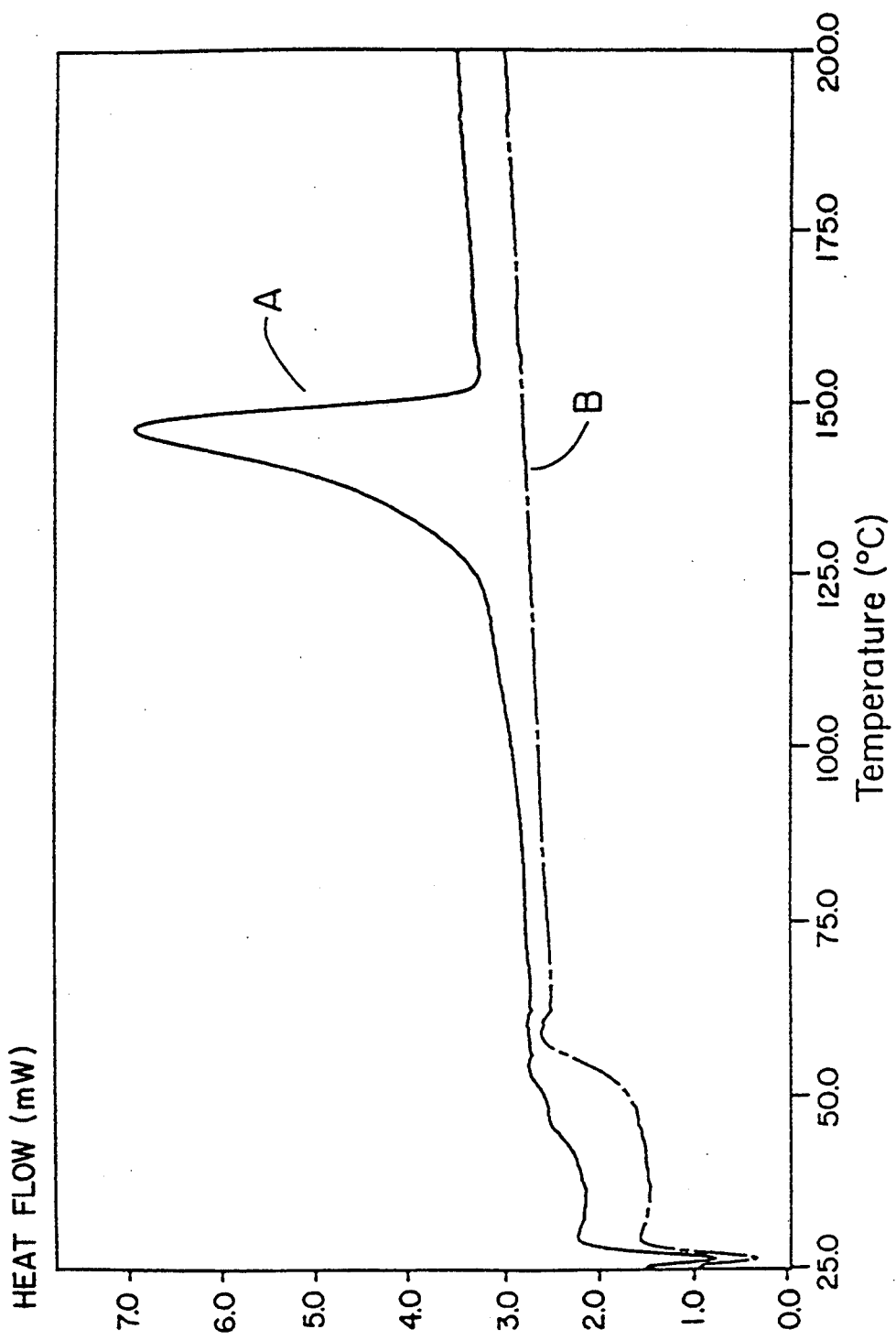
FIG. 6 illustrates a DSC plot for the copolymer of Example 8. A is unquenched while B is quenched.

A DSC of the lactide polymer reveals a strong Tm at 145 C., see FIG. 6. The lactide polymer was melted, quenched, and examined again by DSC to reveal no crystallization or melting points. However, a Tg appears at approximately 50-55 C. The results show the polymer can be crystalline or amorphous, depending on its heat history.

EXAMPLES 9-12

The composition series was extended, using the procedures of Example I except other L- and racemic D,L-lactide ratios were used and heating was 2 hours 125 C.,

TABLE 3-continued

PHYSICAL PROPERTY COMPARISONS

| Property | Poly(lactic acid), Example 3 | Crystal Polystyrene |
|---|---|---|
| | | 1.6 g/10 min.(f) |

(a)Depends on heat history.
(b)Shore D = 97.
(c)DSC, $T_m$ = 125 C. (257 F.) at 10 degree/min.
(d)Flow rate decreases at lower temperature.
(e)Listed by manufacturer.
(f)By our experiment.

EXAMPLE 13

The copolymer of Example 2 was molded and remolded several times to determine if color would develop in the films and the molecular weights remained high. This determines if the copolymer can be recycled, an important consideration for manufacturing practices. The results of Table 4 show that the copolymer remained completely transparent and colorless after repeated heating and molding despite the fact that the copolymer was repeatedly exposed to air at elevated temperatures.

TABLE 4

EFFECT OF MOLDING ON LACTIDE COPOLYMER

| Example No. | History | Appearance | $M_w'$ 1000's | $M_n'$ 1000's | $M_w/M_n$ |
|---|---|---|---|---|---|
| Example 2(a) | Not molded, directly from polymerization | Completely transparent and colorless | 928 | 218 | — |
| Example 13(a) | Ex. 2 after molding(b) | Completely transparent and colorless | 301 | 135 | 2.22 |
| Example 13(a) | Ex. 2 after molding 6 times(b) | Completely transparent and colorless | 137 | 56.7 | 2.42 |

(a)85/15, L-lactide/racemic D,L-lactide copolymer.
(b)Compression molding at 167 C. (333 F.) for 7 minutes to 5-mil film.

EXAMPLES 14–18

The copolymers of Examples 2, 3 and 6 were compression molded into films of approximately 20 to 30-mil thickness and were placed in a heated Instron tester where the films were drawn 5 times their length at 83 C. at a rate of 0.5 inch per minute. The films were cooled quickly upon removal from the Instron, and found to be approximately 5-mil in thickness. They were clear and colorless. Tensile properties were evaluated and are listed in Table 5. When drawn 8 to 10 times their length, the films show evidence of crystal formation by virtue of haze development and some loss of transparency.

The results demonstrate that very thin films can be made with adequate stiffness and transparency for a crystal polystyrene offset. Thus, despite the higher density of the lactide copolymers compared to polystyrene, less material can be used for stiff crystal polystyrene offsets.

TABLE 5

PROPERTIES OF L-LACTIDE/RACEMIC D,L-LACTIDE COPOLYMERS AFTER ORIENTATION(a)

| | Composition, weight Ratio, L-Lactide/ D,L-Lactide (Racemic) | | | | |
|---|---|---|---|---|---|
| | 85/15 | 85/15 | 85/15 | 87.5/12.5 | 95/5 |
| | | | Example Number | | |
| | 14 | 15 | 16 | 17 | 18 |
| Film thickness, mil | 5.5 | 5.0 | 6.5 | 5.0 | 4.0 |
| Tensile strength, 1000 psi | 14.0 | 14.7 | 15.0 | 13.0 | 16.0 |
| Elongation, % | 31.5 | 15.4 | 30.0 | 23.8 | 37.4 |
| Tangent modulus, 1000 psi | — | 564 | 419 | 432 | 513 |

(a)5X oriented at 83 C. using a draw down speed of 0.5 in./min. on Instron.

EXAMPLE 19

Films of the copolymers of lactide of Table 1 were immersed in water for several months interval. The copolymers remained clear for approximately 2 months; after 3 months a slight haziness developed. Upon setting on the shelf in humid air and with frequent handling, the films remain virtually unchanged for approximately 1 year although Instron data will show a slow decrease in the strength and elongation after several months. In a landfill, the buried films disappear in 6 months to 2 years, depending on the moisture, pH, temperature, composition, surface-to-volume ratio, and biological activity of the landfill. All of the films burn with a clean, blue flame.

EXAMPLE 20

The lactide copolymer of Example 5 (quenched, compression-molded film) was examined by DSC and found to have less than 2 percent crystallinity, see FIG. 1, in the vicinity of 130 C. A ⅛ inch thick sample of the copolymer of Example 5 was annealed in a 185 F.. oven for 16 hours. The sample turned hazy and the DSC of the sample, see FIG. 3 revealed a pronounced increase in the crystallinity. The sample showed a 264 psi heat deflection temperature (HDT) of 90 to 95 C. A similar sample without annealing exhibited a heat deflection temperature of 50 to 55 C., which corresponds to its Tg.

EXAMPLE 21

Calcium lactate, 5 weight percent, was blended on a heated mill roll with the lactide copolymer of Example 5 at 170 C. for approximately 5 minutes. The blend was stripped off the roll as a sheet and examined. It was stiff, strong, and hazy. Optical microscopy at 82× reveals heterogeneous domains in the size range of from a few microns to 30 microns. DSC reveals a substantial increase in crystallinity in the vicinity of 145 C., see FIG. 4, which remain on quenching and reheating. The results, above, comparing Examples 8, 20, and 21, show that nucleating agents are more prompt and efficient in inducing crystallinity in lactide copolymers. Nucleating agents such as salts of carboxylic acids may be used, salts of lactic acid are preferred.

EXAMPLE 22

In a 500-ml, 3-neck, round bottom flask, equipped with a mechanical stirrer and a nitrogen inlet and outlet, was placed 180.7 g of L-lactide and 40.2 g of racemic D,L-lactide (both Boehringer and Ingelheim, grade S). The contents of the flask were heated to 110 C. under a nitrogen sweep to melt the lactides and 20.1 g of polystyrene (Amoco R3, melt index 3.5 g/10 min.) was added. The polystyrene swelled highly and partially dissolved with stirring overnight while advancing the heat to 185 C. The temperature was decreased to 141 C. and 0.2 ml of anhydrous stannous octoate solution (0.2 ml/ml of toluene) was added. The stirrer was turned off and the lactides allowed to polymerize at 141 C. over 3 days time. The highly swollen, polystyrene floats to the top after turning off the stirrer. The lower, polylactide phase was cooled and examined by DSC. The sample has a low Tg, approximately 35 C., and is otherwise lacking in apparent temperature transitions. Compression-molded films are clear, colorless, and very pliable. These results indicate that the polystyrene thoroughly interrupts crystallinity formation.

EXAMPLE 23

Figure 7:
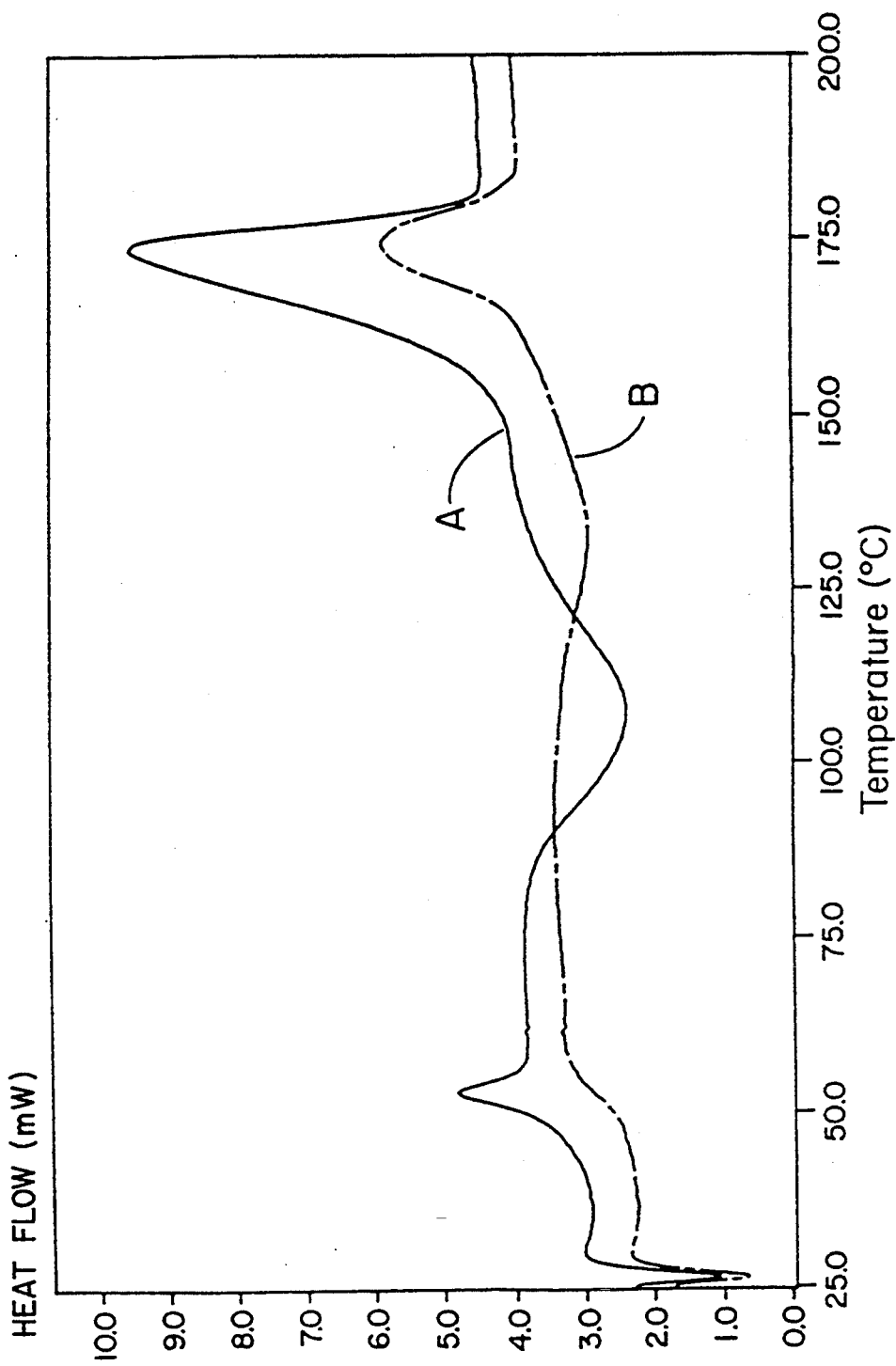
FIG. 7 illustrates a DSC plot for the L-lactide homopolymer that is added to the copolymer of Example 8. A is unquenched while B is quenched.
Figure 8:
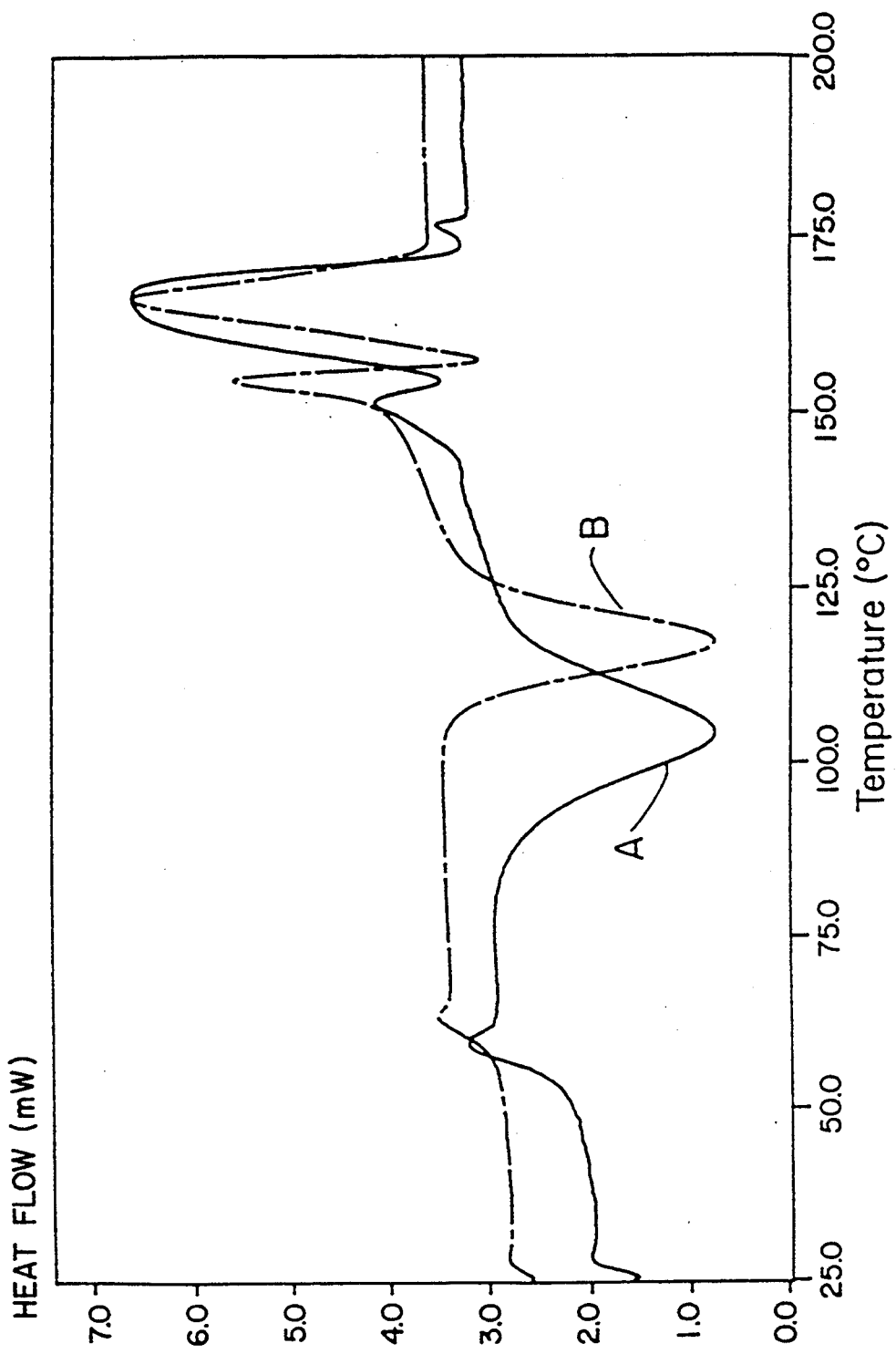
FIG. 8 illustrates a DSC plot for the blended composition of Example 23 of the copolymer of Example 8 and a homopolymer of L-lactide. A is unquenched while B is quenched.

The lactide copolymer of Example 8 was mill-roll blended with 20 weight percent of the homopolymer of L-lactide produced in Example 7. A sample of the homopolymer was analyzed by DSC, see FIG. 7. The blended sample was examined by DSC and found to have a Tg of 59–63 C. and strong Tm's at 150 and 166 C., see FIG. 8. Films were clear to slightly hazy, depending on their cooling rate after pressing. Quenched samples easily crystallize on heating to approximately 80–90 C. As a result the heat deflection temperature of the blend is now quite high. The blend becomes hazy at 80–90 C. but does not deflect with heat as does the unblended 90/10 copolymer. Tensile data as shown in Table 6 were obtained on unoriented, compression-molded films and compared to similarly obtained data for polystyrene.

TABLE 6

COMPARISON OF BLEND OF POLYLACTIDE OF EXAMPLE 23 WITH CRYSTAL POLYSTYRENE

|  | Example 23(a) | Crystal Polystyrene(a,b) |
|---|---|---|
| Film thickness, mil | 8 | 14 |
| Tensile strength, ASTM D882, 1000's psi | 7.7 | 6.0 |
| Elongation, %, to yield | 6.5 | 3.2 |
| Tangent modulus, 1000,'s psi | 323 | 267 |

(a)Thin films, unoriented, compression-molded specimens
(b)Melt Index 1.7

This example illustrates that melt blending is an excellent way to improve the properties of the copolymer so that advantageous properties similar to polystyrene are realized. The higher the amount of homopolymer based on L-lactide (or D-lactide) blended with the polymer the higher will be the heat deflection temperature, however, haziness will also increase. Thus addition of homopolymer may be combined with other methods of increasing polystyrene like properties while still retaining clarity.

As a further example, orienting films produced from the polymer increases the tensile properties. At eight to ten times the draw the physical properties are still increasing but the material becomes hazy. The degree of orientation will thus need to be controlled and combined with the other property changing methods to achieve optimum polystyrene like characteristics.

EXAMPLES 24–27

Examples 24 to 27 were polymerizations of lactide with controlled amounts of chain transfer agents, demonstrating that molecular weights can be controlled using transfer agents such as glycolic acid. The results are shown in Table 7. A nearly straight line relationship exists between the amount of transfer agent and the reciprocal of the weight average molecular weight. Preferred chain transfer agents are lactic acid or glycolic acid.

TABLE 7

MOLECULAR WEIGHT CONTROL USING CHAIN TRANSFER AGENTS

| Example No. | PPH of(a) CTA | $M_n$(b) | $M_w$(b) | $M_w/M_n$ |
|---|---|---|---|---|
| 24 | 0.22 | 13,500 | 107,300 | 8.0 |
| 25 | 0.45 | 12,800 | 66,700 | 5.2 |
| 26 | 0.90 | 7,300 | 29,900 | 4.1 |
| 27 | 1.80 | 4,700 | 13,900 | 2.9 |

(a)Parts of glycolic acid chain transfer agent (CTA) per hundred parts of lactide in polymerization recipe.
(b)Gel permeation chromatography in tetrahydrofuran solvent, 23 C., with $10^6$, $10^5$, $10^4$, and $10^3$ anhstrom columns, number average, $M_n$, and weight average, $M_w$, molecular weights are calculated compared to monodisperse polystyrene standards.

EXAMPLE 28

A 4.0 mil, compression-molded film of the lactide copolymer of Example 2 was evaluated as a barrier film by ASTM methods. The results are shown in Table 8. The lactide copolymer is a much better barrier to carbon dioxide and oxygen than is polystyrene. By comparison to some other polymer barrier films, the lactide copolymer is an adequate barrier film for many packaging applications.

TABLE 8

EXAMPLE 28 PERMEABILITY TO GASES(a)

| Units | Lactide Copolymer, Example 2 | Crystal(b) Polystyrene | Poly(ethylene terephthalate) | Vinylidene(b) Chloride-Vinyl Chloride Copolymer |
|---|---|---|---|---|
| cc/100 sq. in./ 24 hr/atmos | | | | |
| $CO_2$ | 32.1 | 900 | 15–25 | 3.8–44 |
| $O_2$ | 19.9 | 350 | 6–8 | 0.8–6.9 |

(a)ASTM D1434-75, Example 2 was a 4.0 mil, compression-molded film.
(b)Values from Modern Plastics Encyclopedia.

EXAMPLE 29

Sheets, ⅛ inch thick of the lactide copolymers of Examples 1 were immersed overnight in a mixture of petroleum ether and methylene chloride. At ratios of 70/30 to 60/40, petroleum ether/methylene chloride, the copolymers would foam when placed in boiling water. Irregular, but well expanded, foams would form.

Thus, compatible chemical or physical blowing agents may advantageously be used with other processing steps to produce foamed materials. These materials are useful where foamed styrene is typically used (e.g. eating utensils, packaging, building materials and the like). For example, a foaming agent can be added prior to extrusion or injection molding.

EXAMPLE 30

Figure 5:
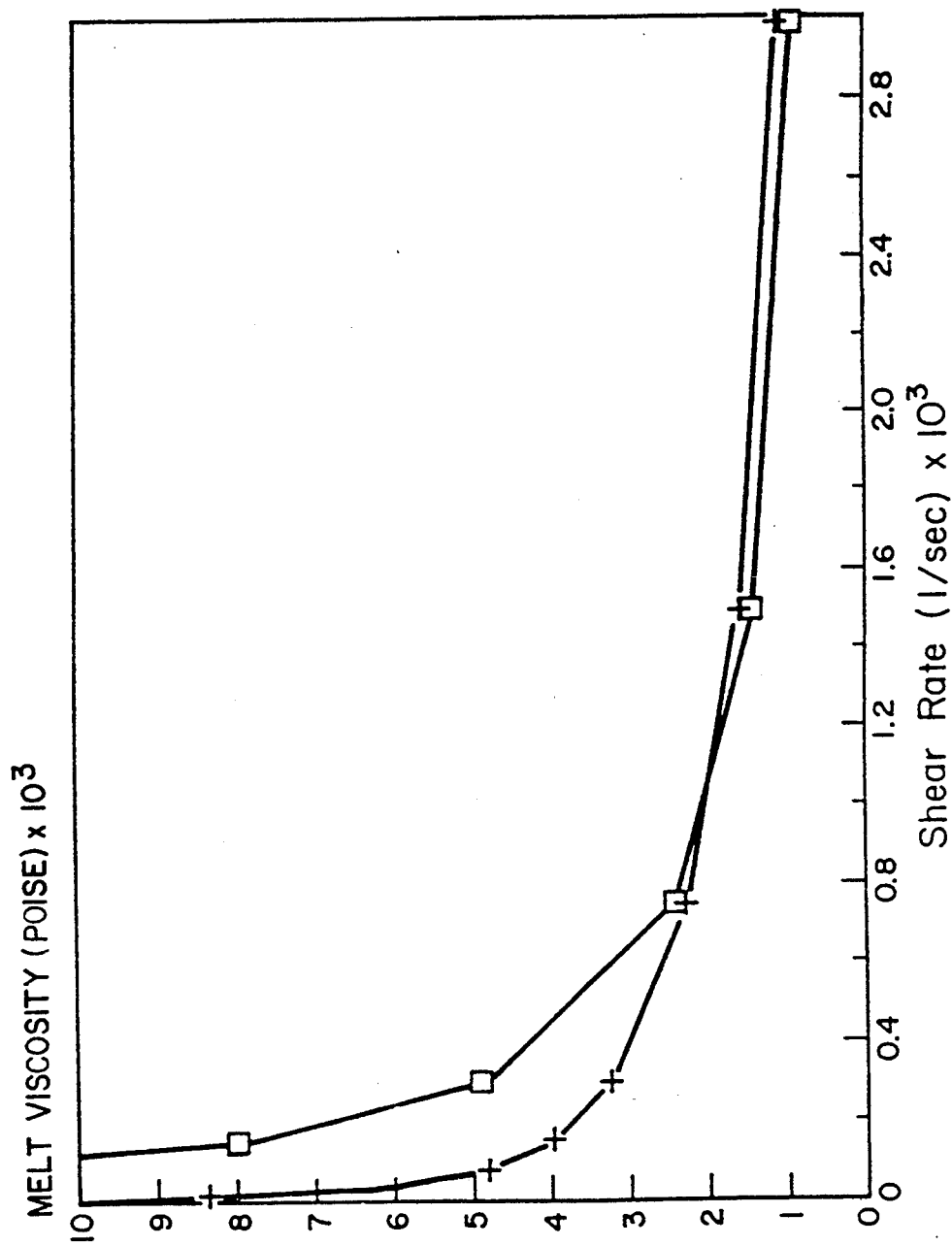
FIG. 5 compares the melt viscosity versus shear rate characteristics of polystyrene (A) at 200 C. and the lactide polymer prepared as in Example 8 (B) at 160 C.

A comparison was made of the melt viscosities of a commercial, crystal polystyrene (Type 201, Huntsman Chemical Corp.) and the lactide polymer of Example 8. The melt index, ASTM D1238 (G), of the polystyrene was 1.6 g/10 min. at 200 C. using the standard 5 Kg weight. The melt index of the lactide polymer was 40–46 g/10 min. under the same conditions, however, at 160 C. the value was 8.0 g/10 min. A more detailed comparison of melt viscosities was obtained by observing the melt viscosities of the two polymers in an Instron Capillary Viscometer. The comparative results are shown in FIG. 5. The shear rates normally encountered during extrusion and injection molding are approximately 100 to 1000 reciprocal seconds. Inspection of the data of FIG. 5 shows that the melt viscosity of the lactide polymer at 160 C. is very similar to that of the polystyrene at 200 C.

The above results illustrate that lactide polymers can be melt-processed, at lower temperatures than polystyrene, by very similar methods.

EXAMPLES 31–34

Small, test polymerizations of purified (recrystallized and dried) mesolactide (meso D,L-lactide) were carried out as the homopolymer and the copolymer. The molecular weights were evaluated by GPC and compared to analogues of D,L-lactide. The results are presented in Table 9. The polymers were melt pressed into films and their physical properties evaluated and compared as shown in Table 10. Within experimental differences of sheet thickness and molecular weight, the copolymers are similar within experimental error. The homopolymer of mesolactide is somewhat weaker.

TABLE 9

GPC MOLECULAR WEIGHT COMPARISONS OF MESO- AND RACEMIC LACTIDE POLYMERS AND COPOLYMERS

| Example Nos. | Composition | Res. Mon., % | $M_n$ | GPC × 10⁻³ $M_w$ | $M_z$ | $M_w/M_n$ |
|---|---|---|---|---|---|---|
| 31* | D,L-PLA | — | 97.5 | 341 | 757 | 3.49 |
| 32 | Meso PLA | 2.76 | 62.5 | 152 | 264 | 2.42 |
| 33 | 90/10, L-/meso | 1.67 | 29 | 142 | 301 | 1.67 |
| 34* | 90/10, L-/D,L | — | 91.3 | 201 | 350 | 2.20 |

*racemic D,L-lactide

TABLE 10

PHYSICAL PROPERTY COMPARISON OF RACEMIC D,L- AND MESO D,L-LACTIDE POLYMERS AND COPOLYMERS(a)

| Example No. | Polymer Composition | Elastic Modulus, 100 psi | Tensile at Yield Strength 100 psi | Elongation to Yield % | Film Thickness, mil | Strain Rate in./min. |
|---|---|---|---|---|---|---|
| 31 | Homopolymer of racemic D,L-lactide | 278 | 5.6 | 2.8 | 5–7 | 0.25 |
| 32 | Homopolymer of meso D,L-lactide | 345 | 3.8 | 3.5 | 9 | 0.25 |
| 33 | 90/10, L-/meso D,L-lactide copolymer | 190 | 7.9 | 3.8 | 12–15 | 0.25 |
| 34 | 90/10, L-/racemic D,L-lactide copolymer | 323 | 8.6 | 4.6 | 4–6 | 0.25 |

(a)Compression-molded films

EXAMPLES 35–47

Figure 9:
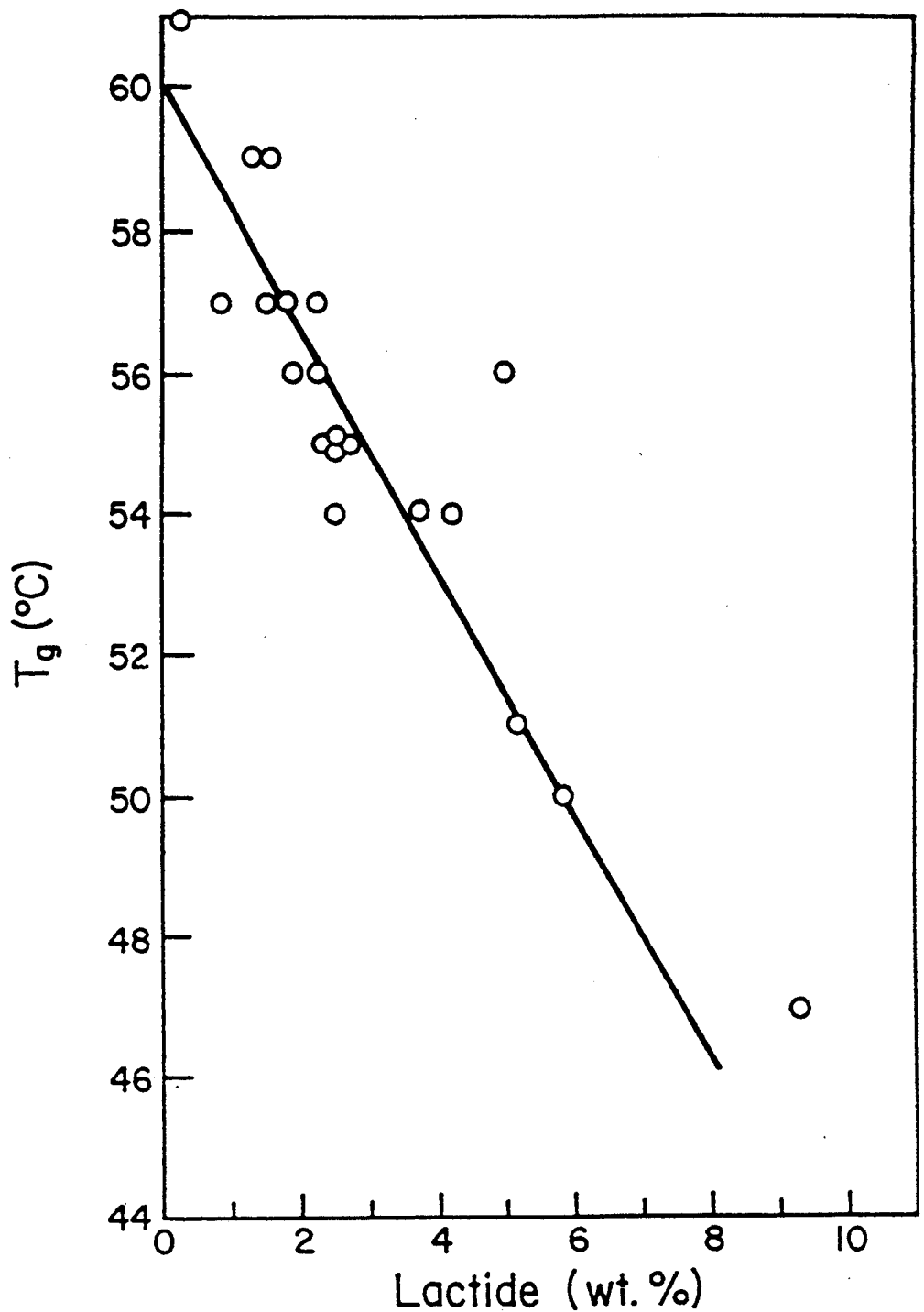
FIG. 9 illustrates a plot of the glass transition temperature of 90/10, L-/D,L-lactide copolymers versus residual lactide monomer.

These examples illustrate the preferred copolymer ratio of the L/D,L polylactide copolymer series (racemic D,L-lactide was used throughout these examples). Of particular interest were the 80/20, 90/10, 95/5, and 100/0 ratios. Each of these copolymers is a material having different properties. Table 11 contains data on the thermal properties of these unoriented copolymers. The glass transition temperature, Tg, varies with the amount of intimately dispersed residual lactide monomer. A typical relationship is shown in FIG. 9 where the residual lactide was measured by TGA and the Tg was estimated by DSC. To a close approximation, the Tg follows this relationship for all of the L-/D,L-lactide copolymer ratios. The 80/20 copolymer typically is an amorphous material with a glass transition temperature of 56 C. This copolymer has limited commercial use since its heat distortion temperature will be on the order of 45–50 C., which is considered too low for many packaging applications which require a rigid polymer used in applications up to 70 C.

The other copolymers have the same or only slightly higher glass transition temperatures, but can be crystallized to improve their thermal stability. The rate of crystallization increases as the D,L content decreases and the molecular weight decreases. From the point of view of thermal properties alone the 100 percent poly(L-lactide) polymer is most desirable. However, when other characteristics such as processability into molded and extruded shapes, the capability to do so at lower temperatures with less viscosity and color formation, discharging a reactor, and transparency are taken into account the preferred ratio is 85/15 to 95/5 as further discussed herein.

TABLE 11

SUMMARY OF THERMAL PROPERTIES OF LACTIDE COPOLYMERS

| Ex. No. | Copolymer Ratio | Glass Transition Temperature C., | Melting Temperature C. |
|---|---|---|---|
| 35 | 80/20 | 56 | — |
| 36 | 90/10 | 55 | 150 |
| 37 | 95/5 | 59 | 164 |
| 38 | 100/0 | 63 | 178 |

The mechanical properties of sheet extruded from each of these copolymers also differs somewhat, depending on copolymer ratio. Table 12 summarizes data that has been obtained on as-extruded and 3× biaxially oriented sheet. The biaxially oriented sheet can be either amorphous or semi-crystalline through crystal growth during annealing. The annealed sheet has been found to be thermally stable up to the annealing temperature, approximately 110 C.

Since the 80/20 copolymer does not crystallize upon annealing, it will always be subject to thermal distortion when heated above its glass transition temperature. Orientation does increase its room temperature mechanical properties to very high levels, however.

The 90/10 copolymer shows an increase in most properties from both annealing and orientation. The oriented and annealed sheet had mechanical properties approximately the same as that of the 80/20 copolymer.

The available data on the mechanical properties of unoriented 95/5 copolymer indicates it is approximately the same strength as the 90/10 copolymer within a generous experimental error, compare, for example, Examples 4, 5, and 6. The mechanical properties of the 95/5 oriented copolymer are not as reproducible as those of either the 80/20 copolymer or the 90/10 copolymer. However, they can be considered acceptable for most applications. The reason for the drop in mechanical properties has been attributed to numerous micro defects found in the oriented sheet. The cause of those defects has never been identified; however, the material is known to craze easily upon crystallizing.

For comparison Boehringer Ingelheim poly(L-lactide), Resomer L214, a polymer with a Mw of 800,000 is shown as Examples 38 and 47. The tensile strength of this polymer is not very different from that of the copolymers examined, but its tangent modulus is considerably higher; however, the values used in the tables were as published values not from the tests used to evaluate the other examples.

TABLE 12

SUMMARY OF MECHANICAL PROPERTIES OF LACTIDE COPOLYMERS

| Ex. No. | Copolymer Ratio | Morphology | Process | Tensile Strength psi | Tangent Modulus psi | Elongation % |
|---|---|---|---|---|---|---|
| 39 | 80/20 | A | E | 7500 | 305,000 | 5.7 |
| 40 | 80/20 | A | O-3x | 12200 | 427,000 | 18.2 |
| 41 | 90/10 | A | E | 8000 | 150,000 | 5.0 |
| 42 | 90/10 | C | E | 8500 | 188,000 | 4.6 |
| 43 | 90/10 | A | O-3x | 11700 | 494,000 | 41.2 |
| 44 | 90/10 | C | O-3x | 10200 | 401,000 | 20.7 |
| 45 | 95/5 | A | O-3x | 9900 | 273,000 | 56.5 |
| 46 | 95/5 | C | O-3x | 8800 | 245,000 | 68.0 |
| 47 | 100/0 | C | M | 9400 | 580,000 | — |

A = amorphous
C = crystalline
E = extruded
M = molded
O = oriented

Rheological analysis of the 90/10, 95/5, and 100/0 copolymers was also made to examine the effect of copolymer ratio on flow properties. Because it has a higher melting point than the copolymers, the 100/0 polymer has to be processed at higher temperatures than the other two materials. With a Mw of approximately 200,000 pure poly(L-lactide) has to be heated to 200 C. in order to have a zero shear melt viscosity below 100,000 poise. By way of contrast, the 95/5 copolymer and 90/10 copolymers having Mw's of 200,000 have zero shear viscosity of 100,000 poise at 175 C. and 160 C., respectively.

EXAMPLES 48–56

Processing aids (plasticizers) are necessary in preventing color during extrusion and compounding. The pure poly(lactic acid) can be substantially heated by the work put into it by a high-shear zone of a twin-screw extruder. An extruder set at 350 F., will work on a high molecular weight poly(lactic acid), with no processing aid, to cause its internal temperature to rise to 390 F., or higher, causing browning of the extrudate. For a high shear extruder this can be prevented using approximately 5 percent lactide incorporated into the polymer. It is presently believed that the processing aid acts as a lubricant to prevent discoloration. Other processing aids such as calcium lactate, sodium stearate, and sodium benzoate also are effective. Some illustrative results are shown in Table 13. To those skilled in the art it will be obvious that the exact amount of processing aid will depend on the molecular weights of the poly(lactic acid) and the amount of shear mixing imposed.

Examples 53 and 54 were discolored because they slightly heat-degraded during compounding. For the above examples, using lactide as processing aid (plasticizer), about 5 percent lactide was required as a minimum processing aid to obtain a colorless product. It is noted that other processing aids such as sodium benzoate and calcium lactate obtain colorless extrudates when used in lower amounts.

TABLE 13

USE OF PROCESSING AIDS

| Example | Copolymer[a] Composition | Processing Aid Type | Processing Aid Wt. % | Melt Zone[b] Temp. F. | Color of Extrudate |
|---|---|---|---|---|---|
| 48 | 95/5 | Lactide | 15.5 | 391 | Colorless |
| 49 | 90/10 | Lactide | 15.0 | 381 | Colorless |

TABLE 13-continued
USE OF PROCESSING AIDS

| Example | Copolymer[a] Composition | Processing Aid Type | Wt. % | Melt Zone[b] Temp. F. | Color of Extrudate |
|---|---|---|---|---|---|
| 50 | 90/10 | Lactide | 12.4 | 385 | Colorless |
| 51 | 92.5/7.5 | Lactide | 8.1 | 374 | Colorless |
| 52 | 90/10 | Lactide | 6.5(c) | 381 | Colorless |
| 53 | 90/10 | Lactide | 4.6 | 390 | Slightly brown |
| 54 | 90/10 | Lactide | 3.4 | 404 | Brown |
| 55 | 90/10 | Sodium benzoate | 2.0 | 378 | Colorless |
| 56 | 90/10 | Calcium lactate | 2.0 | 384 | Colorless |

[a]Monomer ratio, L-/racemic D,L-lactide
[b]Temperature at high-shear zone in twin-screw extruder

EXAMPLE 57

Examples 57 to 75 teach the incorporation of lactide in conjunction with quenching to obtain pliability and transparency. Alternatively, the polymers can be annealed to improve stability against heat distortion.

Poly(L-lactide) was prepared by methods previously described. Thus 300 g of triply recrystallized and thoroughly dried L-lactide was loaded into a clean, flame-dried, argon-cooled, 500 ml round-bottom flask. The flask was fitted with a rubber septum and inlet and outlet syringe needles that admitted a continuous argon purge. Stannous octoate solution was prepared by dissolving 20 g in 110 ml of toluene, previously dried over molecular sieves, then distilling 10 ml toluene in order to azeotropically dry the solution. The final concentration was 0.2 g/ml stannous octoate in toluene. A 0.3 ml quantity was injected through the septum onto the L-lactide. The flask and its contents were placed in a 150 C. oil bath, and when melted, swirled vigorously to obtain a homogeneous mix. The argon purge continued and a thermocouple was fitted through the septum into the melt. The melt was 143 C. The temperature of the oil bath was advanced to 200 C. and heating and light purge continued for 20 hours. The temperature of the melt advances to 170–174 C. in the first two hours of heating. The final temperature was 170 C. After 20 hours of heating the flask was cooled in air to room temperature and the solid polymer was transparent.

Polymer was recovered by shocking the flask with dry ice to free it from the glass. The residual monomer was analyzed by thermogravimetric analysis and the molecular weights by gel permeation chromatography. Differential scanning calorimetry reveals a glass transition temperature ($T_g$) at 53 degrees and two melting point endotherms with peaks at approximately 170 and 190 C. The gel permeation chromatography molecular weights: $M_n=129,000$; $M_w=268,000$; $M_z=462,000$; $M_w/M_n=2.08$. Residual monomer by thermogravimetric analysis was 2.3 percent, (Example 57, Table 14.) The experiment shows that L-lactide can be polymerized above, or near, its melting point and the products remain transparent and more amorphous.

EXAMPLE 58

By methods similar to Example 57, 104.0 g of L-lactide was polymerized using 0.10 ml of stannous octoate catalyst solution. However, the reaction temperatures were 155°165 C. for 72 hours. The polymer (No. 58 of Table 14) slowly crystallizes upon forming and is a white opaque solid at reaction or room temperature. Since the sample was smaller than that formed in the preceding experiment, the polymer cooled more quickly, but it did not quench to a transparent solid. In comparison to Example 57, the lower reaction temperature permits the poly(L-lactide) to crystallize and become opaque, thus an intimate dispersion of plasticizer does not form.

The temperature is slowly advanced in many of these experiments to accommodate the polymerization exotherm. The reaction temperature must reach at least 170–175 degrees prior to a substantial monomer-to-polymer conversion, otherwise the poly(L-lactide) crystallizes and is difficult to remelt.

In Examples 60–66 the polymerization of L-lactide was repeated varying the conditions to obtain poly(L-lactides) with different residual lactide contents and crystallinities. The results are shown in Table 11, where it is seen that pliability and toughness were obtained only when the product has been quenched from the melt, is transparent at room temperature, and contained approximately 10 percent or more residual lactide. It is believed that the L-lactide homopolymer must be polymerized in the melt, and quenched from the monomer-polymer melt temperatures, to a transparent material as evidence of its homogeneous and intimately plasticized properties. When the poly(L-lactide) crystallizes during polymerization because the polymerization temperature is well below the polymer's melting point, the residual monomer is no longer effective as a plasticizer. If the polymer crystallizes upon cooling to room temperature, it also loses its plasticization. Annealing at elevated temperatures will restore crystallinity to amorphous samples.

TABLE 14
POLYMERIZATION OF L-LACTIDE

| Ex. No. | Catalyst Amount pph | Temp C. | Time, hours | Polymer Appearance | Residual Monomer Percent | Sample Size g |
|---|---|---|---|---|---|---|
| 57 | 0.02 | 156–201[a] 150–174[b] | 20 | clear transparent, hard, glassy | 2.30 | 300 |
| 58 | 0.02 | 155–165[a] | 72 | crystalline, opaque, hard brittle | — | 104 |
| 59 | 0.005 | 120–200[a] 111–200[b] | 24 | crystalline, opaque, hard, brittle | — | 100 |
| 60 | 0.02 | 135–145[b] 135–152[b] | 22 | crystalline[d], opaque, hard, brittle | 1.1 | 500 |
| 61 | 0.02 | 117–185[a] 120–175[b,c] | 24 | crystalline, opaque, hard, brittle | 1.74 | 100 |
| 62 | 0.02 | 160–170[a] | 8 | crystalline | 2.18 | 2,000 |

TABLE 14-continued
POLYMERIZATION OF L-LACTIDE

| Ex. No. | Catalyst Amount pph | Temp C. | Time, hours | Polymer Appearance | Residual Monomer Percent | Sample Size g |
|---|---|---|---|---|---|---|
| 63 | 0.02 | 145[a] 137-144[b] | 15 | opaque, hard brittle crystalline, opaque, hard, brittle | 3.6 | 25 |
| 64 | 0.0553 | 190[a] 160-215[b] | 0.3 | clear, pliable tough, transparent | 10.1 | 25 |
| 65 | 0.0553 | 188-193(8) 147-200[b] | 0.28 | clear, transparent, pliable except at edge of polymerizate | 22.9 | 25 |
| 66 | 0.02 | 145[a] 150-133[b] | 2.75 | crystalline[d], opaque, hard brittle | 52.5 | 25 |

[a] Oil bath temperature.
[b] Polymer melt temperature.
[c] This polymer crystallized at 160-169° as the temperature was advanced and it did not remelt.
[d] Transparent at reaction temperature, crystallizes upon cooling.

This transparency and intimacy of association between polymer and monomer is also affected by the ratio of L/D,L-lactide. At approximately 95/5 ratio the copolymer easily quenches to a transparent solid. The 90/10 ratio, L/D,L-lactide copolymer quenches quite easily. The 100 percent L-lactide polymer quenches with difficulty from thick sections of the polymer to a transparent material. Some comparisons are shown by Examples 67-71 of Table 15. Thinner cross sections, i.e., films of the L-lactide polymer can be plasticized and quenched to pliable and transparent materials. The 80/20 copolymer quenches very easily to a transparent solid. The latter has only a trace of crystallinity as seen by differential scanning calorimetry.

TABLE 15
TRANSPARENCY OF LACTIDE POLYMERS

| Ex. No. | Lactide L/D,L- Ratio | Temp. C.[a] | Time, hours | O/T[b] | GPC $M_w$ | Residual Monomer, percent |
|---|---|---|---|---|---|---|
| 67 | 95/5 | 145-160 | 67 | SO | 385,000 | 2.64 |
| 68 | 100 | 135-152 | 22 | O | 322,000 | 1.1 |
| 69 | 90/10 | 150-157 | 45 | T | 821,000 | 4.95 |
| 70 | 90/10 | 150-170 | 48 | T | 278,000 | 1.37 |
| 71 | 80/20 | 135-175[c] | 23 | T | — | — |

[a] Melt temperature (polymerization temperature).
[b] Opaqueness/Transparency (O/T) after air-cooling of polymerizates; opaque (O), slightly opaque (SO), transparent (T).
[c] Slow-cooled for 1 hour.
All D,L-lactide is racemic.

All of the lactide polymers thermoform easily, that is, when heated by a radiant heater until soft, then sucked down on an intricate mold, they all form the pattern of the mold easily. However, the poly(L-lactide) becomes partially cloudy and hazy upon cooling. The 95/5, 90/10, and 80/20 copolymers are quite clear and transparent throughout their thermoforms.

EXAMPLE 72

The poly(L-lactide) from Example 57 was melted and mixed on an open 2-roll mill for 5 minutes at 375 F. (190 C.), then compression molded at 375 C. for 2 minutes, then air-quenched to room temperature in approximately 30 seconds. Both 7-and 20-mil thick films were prepared. Both were clear and transparent without trace of haze or opacity. Residual monomer in the film was 0.79 percent. The films are very stiff.

EXAMPLE 73

The experiment was repeated except that the milling was continued for 10 minutes instead of 5 minutes. The films were analyzed by thermogravimetric analysis again and found to have 0.38 percent lactide. The films were clear, transparent, and stiff.

EXAMPLE 74

The mill-rolled polymer was also compression molded into a ¼×¼×1 inch plaque. This plaque required 5-10 minutes to cool in the press by turning on the cooling water to the press. The plaque was white, opaque, and crystalline except for the extreme edges, which were transparent.

The above Examples 72-74 teach the quenching of films of poly(L-lactide) to maintain transparency. When cooled more slowly, they crystallize and lose their transparency.

Quenching as used herein indicates that the temperature is dropped rapidly to prevent extensive crystallization of the polymer. Crystallization of polymers is a slow process, requiring minutes to hours to fully accomplish. When this is desired, the temperature is held above the glass-transition temperature, Tg, for some time to allow the molecules to order themselves into extensive crystalline lattices. This is called annealing. When cooled rapidly from an amorphous melt, the polymer does not have the time required and remains largely amorphous. The time required to quench depends on the thickness of the sample, its molecular weight, melt viscosity, composition, and its Tg, where it is frozen-in as a glassy state. Note that melt viscosity and Tg are lowered by plasticization and favor quenching. Thin films obviously cool very quickly because of their high surface-to-volume ratio while molded items cool more slowly with their greater thicknesses and time spent in a warm mold before removal. Regular structures such as poly(L-lactide) order more easily and crystallize more quickly than more random structures such as a copolymer.

With the polylactides the melting points are approximately 150-190 C. depending on the L-lactide content and, therefore, the regularity of structure. The Tg of all the polylactides, including various L and D,L homopolymers and copolymers is 60 C. The Tg decreases when residual lactide is intimately dispersed with the polymer. Quenching to an amorphous state requires that the polymer or copolymer in an amorphous melt is rapidly cooled from its molten state to a temperature below its Tg. Failure to do so allows spherulitic crystallinity to develop, that is, crystalline domains of submicron to micron size. The latter scatters light and the polymer specimens become opaque. These crystalline forms have improved stability to heat distortion. This spherulitic crystallinity is often called short range order-long range disorder since the crystallites are separated by amorphous regions. However, the crystallites act as pseudo crosslinks to maintain dimensional stability above the Tg but below their melting points. Alternatively stability to heat distortion can be obtained by orienting an amorphous polymer above its Tg but below its melting point. Here, the polymer molecules are stretched to allow some long range ordering, then "heat set" to permit the ordering to complete, that is, given some time to anneal. The amorphous polymer is thereby crystallized into a different order, called long-range order, short range disorder. Transparency and resistance to heat distortion are favored.

A detailed discussion can be found in textbooks, for example, "Structural Polymer Properties", by Robert J. Samuels, Wiley Publications, N.Y., N.Y. 1974.

As D,L-lactide is introduced as a comonomer, quenching can be replaced by ordinary cooling to retain transparency. Spherulitic crystallinity can be introduced into these films by annealing and the 100 percent L-lactide polymer is the fastest to crystallize. Where transparency is not required the higher L-lactide polymers can be annealed to greatly improve their resistance to thermal distortion. Conversely, where transparency is required, such as in a crystal polystyrene offset, great care must be taken to avoid this type of opaque crystallinity.

EXAMPLE 75

The poly(L-lactide) film samples were annealed on a hot plate at 240 F. (115 C.). The film turned hazy in approximately 1 minute and completely cloudy in approximately 2 minutes. By way of comparison, a 90/10, L/D,L-lactide copolymer film required 10 minutes to turn hazy, 15 minutes to become completely cloudy. When suspended by one end horizontally in an oven and advancing the temperature slowly, the annealed poly(L-lactide) sample remained straight until a temperature of 295 F. (146 C.) was obtained. The film then bent over. The annealed 90/10 copolymer bent over at a temperature of 185 F. (85 C.). The results show that the amount of crystallinity of polylactides can increase their form-stability at elevated temperatures to a temperature that is well above their $T_g$.

EXAMPLES 76-79

The following examples illustrate the beneficial effects of adding lactide during compounding. The examples show that without lactide as modifier, the lactide polymer degrades during compounding. With the addition of lactide both discoloration and molecular weight decrease are prevented or substantially reduced during compounding.

Thus, in Example 76, a 90/10, L-/D,L-lactide copolymer prepared as described by previous methods using 0.02 pph $SnCl_2 \cdot 2H_2O$ catalyst was ground and extruded into pellets from a twin screw compounder, adding 5 weight percent lactide. The melt zone temperature of the extruder rose to 390 F., the polymer discolored, and the weight average molecular weight ($M_w$, by gel permeation chromatography) decreased by approximately 40 percent. The results indicated that insufficient lactide was added for this very high $M_w$ copolymer. The results are shown in Table 16. The pellets from this compounding were recompounded adding a further 10 weight percent lactide (Example 78). The melt zone temperature was 375 F., and the results were much better: further discoloration did not occur, molecular weight decreased slightly, or within experimental error, and a pliable composition was obtained.

TABLE 16

EFFECT OF LACTIDE AS MODIFIER DURING COMPOUNDING

| Ex. No. | Color | $M_w{}^{(a)}$ | $M_w/M_n{}^{(a)}$ | Lactide$^{(b)}$ weight percent |
|---|---|---|---|---|
| | Before Compounding | | | |
| 76 | light yellow | 513 | 2.15 | 0.78 |
| 77 | light yellow | 278 | 1.80 | 1.37 |
| | After Compounding | | | |
| 76 | dark yellow | 322 | 2.05 | 5.56$^{(c)}$ |
| 77 | yellow | 184 | 1.90 | 2.26 |
| 78 | dark yellow | 307 | 2.00 | 14.4(d) |
| 79 | colorless$^{(e)}$ | 324 | 1.99 | 14.6 |

$^{(a)}$GPC × $10^{-3}$.
$^{(b)}$By thermogravimetric analysis, at 200° C.
$^{(c)}$Five weight percent lactide added during compounding.
$^{(d)}$Further 10 weight percent lactide added during compound.
$^{(e)}$Thin film.

To ascertain that the second compounding and extrusion were facilitated due to the lactide modifier and not the decreased molecular weight, another compounding (Example 77) was performed starting with a similar-$M_w$ copolymer of 90/10, L-/D,L-lactide. In this case, no lactide was added back in during the compounding. The melt zone temperature was 382 F., the copolymer was discolored, and the $M_w$ decreased by approximately 66 percent. In addition, approximately 5 percent more torque was required to compound the mix of $M_w$ 278,000 as compared to the one of $M_w$ of 322,000 with added lactide.

After compounding twice with lactide, Example 78 was analyzed by thermogravimetric analysis and found to have a lactide content of 14.4 percent. The material of Example 78 was converted to a blown film by means of a Haake-Brabender extruder in Example 79. Thin films of this composition are colorless, highly transparent, and very pliable and extensible as described below in Examples 60-64. The Mw by gel permeation chromatography was 324,000 (cf. Mw=307,000 before compounding and extrusion). The Tg of this plasticized material is 42 C. and differential scanning calorimetry reveals a very small amount of crystallinity melting at approximately 138 C. The amount of lactide present is 14.6 percent as estimated by thermogravimetric analysis.

EXAMPLES 80 AND 81

The compounded polylactides, Example 76 and 77, were mixed together in the twin-screw compounder with extra lactide to raise the lactide level to approximately 20 percent. The compounding temperature was 347 F. (175 C.), much reduced from the previous 375 to 385 F. The compounding proceeded smoothly without further discoloration.

The above results clearly show the beneficial effects of added lactide as modifier. The required torque to compound the compositions, the discoloration, and the working temperature are decreased when adding lactide. Further evidence of plasticization is seen in the lowered Tg and the pliability of the compositions. In addition, molecular weight decreases are avoided and stable compositions are obtained. It will be obvious to those skilled in the art that the amount of lactide employed depends on many factors, including the desired amount of plasticization sought, the type of compounder that is used, and the molecular weight of the polylactides.

EXAMPLES 82 TO 86

These examples illustrate plasticization with oligomeric esters of poly(lactic acid). Copolymers of 90/10, L-/racemic D,L-lactide were melt blended with added lactide, esters of oligomeric/lactic acid, and mixtures thereof. They were characterized by tensile and thermal properties.

In Example 82, a control copolymer of 90/10, L-/racemic D,L-lactide was assayed by thermogravimetric analysis to be 6.74 percent lactide. This was mixed with 30 percent by weight oligomeric poly(methyl lactate) (Mella) in Example 83, which was prepared by heating 2,500 g of (S)-methyl lactate in an autoclave at 210 C. for 3 hours, then collecting the Mella which fractionally distilled at 81 to 85 C./1.25 torr. The mixture was melt blended on an open 2-roll mill at approximately 350 F. The blend was compression molded in a press at approximately 350 F. into clear, pliable films. The tensile properties, before and after, adding the Mella are recorded in Table 17. The glass transition temperature (Tg) was reduced by the Mella plasticizer.

For Example 84, the 90/10, L-/racemic D,L-lactide copolymer was melt blended with added L-lactide in a twin screw extruder to adjust the L-lactide content to 20 percent by weight. The blend was further mixed with oligomeric poly(ethyl lactate) (Ella) (Example 85) and Mella (Example 86). The properties of these blends are also recorded in Table 17.

TABLE 17

CHARACTERISTICS OF POLYLACTIDES[a] PLASTICIZED WITH OLIGOMERIC ESTERS OF LACTIC ACID

| Ex. No. | Plasticizer | Elastic Modulus psi | Break Strength psi | Strain at Break, % | $T_g$[b] | $T_m$[c] |
|---|---|---|---|---|---|---|
| 82 | 6.74%[d] L-lactide | 370,000 | 6,903 | 2 | 51 | 141 |
| 83 | 6.74%[d] L-lactide and 30% Mella[e] | 154,000 | 2,012 | 100 | 30 | 141 |
| 84 | 20% L-lactide | 101,000 | 2,637 | 278 | — | — |
| 85 | 20% L-lactide and 30% Ella[f] | 7,316 | 2,561 | 339 | — | — |
| 86 | 20% L-lactide and 30% Mella[e] | 3,620 | 495 | 83 | — | — |

[a]90/10, L-/racemic D,L-lactide copolymer.
[b]Glass transition temperature.
[c]Melting point.
[d]Analyzed by thermogravimetric analysis.
[e]Methyl lactate oligomer.
[f]Ethyl lactate oligomer.

EXAMPLES 87 to 92

These examples illustrate the injection molding of polylactide copolymers and the process for increasing their heat distortion temperature. 90/10 L-/racemic D,L-lactide copolymer (about 1.3 weight percent residual monomer) was injection molded on a New Britain injection molding machine having 75 tons of clamping capacity and a maximum shot size of 6 ounces. Standard ASTM D-638 tensile bars were molded during these trials. The molding conditions were varied over a range of conditions. The polymer, having a weight average molecular weight of 350,000 was successfully molded to melt temperatures between about 165 and 200 C. Polymers with lower molecular weights were more easily molded. The temperature of the mold ranged between about 23 and about 85 C., and the time at which the polymer was held in the mold after filling, but prior to ejection, was varied between about 10 seconds and about 2 minutes.

Calcium lactate, at a 1 weight percent concentration, was compounded into the polymer before injection molding. This was done to provide nucleation sites to increase the rate of crystallization. Crystallization in the injection molded parts was desirable to increase the heat distortion temperature of the polymer.

For example, molded parts of the nucleated 90/10 copolymer, were annealed between metal plates at about 110 C. for times between about 30 seconds and about 4 minutes. After examining the DSC curves of the annealed parts for the presence and degree of crystallinity, it was found that annealing times between about 1 and 2 minutes were required to develope full crystallization when the polymer is in contact with solid walls at 110 C. Mechanical properties of injection molded samples are shown in Table 18. This table shows that annealing does affect the heat distortion temperature, but does not strongly influence the strength, modulus, or elongation to break. The heat distortion temperatures listed in this table were obtained under a load of 264 psi. If a 66 psi condition had been used to determine heat distortion temperatures, the increase observed for the annealed sample would have been even greater.

TABLE 18

MECHANICAL PROPERTIES OF INJECTION MOLDED POLYLACTIDE

| Example Number | Process | Strength, psi | Modulus, psi | Elongation, percent | HDT, C |
|---|---|---|---|---|---|
| 87 | Injection | 8600 | 230,000 | 6 | 46 |
| 88 | Injection/ annealed | 8700 | 258,000 | 4 | 57 |

Calcium lactate-nucleated polymer was injection-molded with a mold maintained at about 85 C. and holding times of about 2 minutes. These conditions were insufficient to develop full crystallinity in the sample. The mold heating system was improved to provide in mold annealing at temperatures higher than 85 C., most preferably between about 110 and about 135 C.

Samples were also injection molded using a melt blend of the 90/10 L-/racemic D,L-lactide copolymer and about 5 to about 20 weight percent poly(L-lactide) as nucleating agent. The results are shown in Table 19. The injection molded specimens were well formed with excellent strengths, stiffness, and impact resistance. The heat distortion temperatures shown in Table 19 can be improved by annealing.

TABLE 19

PROPERTIES OF INJECTION MOLDED BIODEGRADABLE POLYMER

| Ex. No. | Formulation[a] 90/10 % | L-PLA % | Tensile Strength psi | 1% Secant Modulus psi | Strain to Break % | HDT 264 psi F | Izod Impact ft-lb/in. |
|---|---|---|---|---|---|---|---|
| 89 | 95 | 5 | 8,245 | 227,440 | 7 | 115 | 0.34 |
| 90 | 90 | 10 | 8,325 | 221,750 | 7 | 117 | 0.34 |
| 91 | 85 | 15 | 8,631 | 230,150 | 7 | 116 | 0.35 |
| 92 | 80 | 20 | 8,615 | 228,840 | 6 | 117 | 0.35 |

[a]90/10 = 90/10, L-/racemic D,L-lactide copolymer; L-PLA = 100 percent L-lactide polymer.

EXAMPLES 93 to 109

Comparative Examples 93 to 109 were selected from the patent literature that presented conditions most likely to result in materials of the invention. The materials produced in these patents were not completely characterized, thus experiments were needed to allow a more complete characterization of the examples and provide meaningful comparisons that would demonstrate that the materials of the present invention are indeed novel. With regard to the present invention, compositions were sought that had residual lactide or lactic acid contents of about 0.1 to about 60 weight percent and in addition may have the lactide or lactic acid intimately dispersed within the polymer. The results fall into obvious categories. Thus, products with number-average molecular weights, $M_n$, less than 32,000 do not have the physical properties required in the present invention. In fact films from these low $M_n$ compositions were too brittle to be handled for tensile measurements.

It is known from the teachings herein that lactic acid, lactide or oligomers of lactide or lactic acid, or derivatives of lactic acid must be present to provide plasticization and the advantages of the invention. The plasticizer must be present in amounts greater than about 0.10 weight percent up to about 10 weight percent. Thus, if the plasticizer is intimately dispersed and effectively mixed, the composition is substantially transparent. The heterogeneous domain size of the lactic acid, lactide, oligomer, or oligomeric derivative is small enough, generally less than one micron, so that it will no longer scatter light, i.e., it is intimately dispersed. Conversely, white opaque samples are always hard because they have crystallized under the test conditions. Crystallization squeezes the lactide out of the polymer mass, resulting in hard stiff compositions that are a gross mixture of monomer and polymer. This is also obvious from differential scanning calorimetry (DCS) measurements. Monomeric lactide that has segregated reveals itself with a separate melting point at 95 to 100 C., whereas well-plasticized samples do not show a distinct monomer melting point.

One very important point is that the cited patents frequently specify L-lactide homopolymer ("100 percent L-" in Tables 20A and 20B). The homopolymer of L-lactide easily crystallizes because of its high melting point. At lower reaction temperatures, the homopolymer can retain appreciable quantities of monomer, but the composition freezes during polymerization. At higher, melt temperatures, the L-lactide polymerizes so quickly that it is very difficult to stop the polymerization with substantial monomer left in the product. This is true to a lessor extent for poly(L-/D,L-lactide) copolymers also.

Inspecting the results listed in Table 20A and 20B reveals that the comparative examples obtain either products with low residual lactide, or products with residual lactide that is not intimately dispersed as seen by their color, opaqueness, and crystallinities. Thus, Example 94 (very similar also to the work of Schneider), obtained no residual lactide while Example 97 had 4.6 weight percent residual lactide, and both were off colored products. The best known laboratory techniques were added to the procedures, described in the footnotes, for these examples, from a historical standpoint (monomer purity, for example) in an effort to make the procedures work, with indifferent success. Either glassy, or hard, crystalline, opaque products were obtained. It should be noted that only those examples using tin compounds as catalysts appear to be acceptable for many packaging applications.

It appeared particularly that the methods of U.S. Pat. No. 2,758,987 and U.S. Pat. No. 4,137,921 would provide the materials of the present invention. To ascertain this, it was necessary to do the listed experiments on their teachings in detail as shown in Examples 94 and 97. Preparations according to the exact replication of the methods were performed. Thermogravimetric analysis reveals 0.0 percent residual lactide for one such preparation, Example 94. Whereas this polymer was light yellow and contains no detectable residual lactide, the composition of the present invention is colorless and contains small amounts of lactide as a processing aid to prevent color formation during melt fabrication.

A colored product was obtained repeating the teachings of Example 97. The residual monomer analyzed as 4.6 percent lactide. The material was light yellow, presumably due to the high polymerization temperature which produced color bodies with the lactide polymer, the dioxane solvent, and stannous octoate.

TABLE 20A

RELATED ART POLYMERIZATIONS OF LACTIDE CONDITIONS

| Ex. No. | Patent | Patent Example | Lactide Monomer(s) | Catalyst Type | pph | Polymerization Temp. C. | hours |
|---|---|---|---|---|---|---|---|
| 93 | U.S. Pat. No. 2,758,987 | 1 | L- | PbO | 0.30 | 150 | 42 |
| 94 | U.S. Pat. No. 2,758,987 | 3 | 50/50 L-/D,L | PbO | 3.00 | 150 | 89 |
| 95 | U.S. Pat. No. 3,982,543 | 3 | L- | PbO | 0.30 | 150 | 31 |
| 96 | DD 14548 | 2 | L- | SnO[a] | 0.009 | 193 | 3 |
| 97 | U.S. Pat. No. 4,137,921 | 4 | 90/10 L-/DL | Sn(Oct)$_2$ GA/dioxane[b] | 0.0553 | 180 190 | 0.33 0.33 |

TABLE 20A-continued

RELATED ART POLYMERIZATIONS OF LACTIDE CONDITIONS

| Ex. No. | Patent | Patent Example | Lactide Monomer(s) | Catalyst Type | pph | Polymerization Temp. C. | hours |
|---|---|---|---|---|---|---|---|
| | | | | | | 210 | 0.33 |
| 98 | GB 755,447 | 4 | D,L | ZnO[c] | 0.02 | 150 | 24 |
| 99 | GB 755,447 | 2 | D,L | Zn Powder(d) | 0.02 | 140 | 25.5 |
| 100 | GB 755,447 | 6 | D,L | Zn Carbonate Hydroxide[c] | 0.02 | 140 | 2 |
| | | | | | | 150 | 3 |
| 101 | CA 932,382 | 1 | D,L | Tetraphenyl Tin | 0.02 | 165 | 20 |
| 102 | CA 923,245 | 1,7 & 8 | L- | $Et_2Zn$ | 0.167 | 105–110 | 2 |
| 103 | DE 946,664 | 2 | D,L[e] | $ZnCl_2$ | 0.25 | 140 | 48 |
| 104 | DE 1,112,293 | 1 | L- | Sn Stearate | 0.0087 as Sn | 205–210 | 0.5 |
| 105 | U.S. Pat. No. 2,951,828 | 1 | L-[f] | $SnCl_4$ suspension[g] | 0.30 | 160 | 5 |
| 106 | U.S. Pat. No. 3,268,487 | 2 | D,L | Tris(2-chloroethyl)amine[h] | 0.88 | 80 | 24 |
| 107 | EP Applic. 108,635(1984) U.S. Pat. No. 4,550,449; U.S. Pat. No. 4,539,981 | 6, Polymer 8 | L- | $Sn(Oct)_2$ | 0.00108 | 165 | 93 |
| 108 | U.S. Pat. No. 4,539,981 & U.S. Pat. No. 4,550,449 | Polymer 33 | L- | $Sn(Oct)_2$ | 0.00119 | 136–139 | 64 |
| 109 | U.S. Pat. No. 4,539,981 & U.S. Pat. No. 4,550,449 | Polymer 37 | L- | $Sn(Oct)_2$ | 0.00324 | 115 | 64.5 |

[a]No reaction until recipe was changed by adding 0.75 pph of 88 percent lactic acid. Product was white, opaque, very hard and brittle; film too brittle to handle.
[b]Included was glycolic acid as chain transfer agent.
[c]Insoluble.
[d]Insoluble after 24 hours plus additional 1.5 hours with 700 μl 88 percent lactic acid and 100 μl $H_2O$.
[e]In Toluene; product colorless and very viscous.
[f]In mineral spirits, Stoddard solvent No. R-66.
[g]Agglomerated.
[h]In dioxane containing 0.517 pph KOH; no polymerization.

TABLE 20B

RELATED ART POLYMERIZATIONS OF LACTIDE RESULTS

| Ex. No. | Residual Monomer, Percent | $GPC \times 10^{-3}$ $M_n$ | $M_w$ | $M_z$ | $M_w/M_n$ | Polymerizate Appearance |
|---|---|---|---|---|---|---|
| 93 | 0 | 254 | 454 | 717 | 1.79 | Light yellow, crystalline, opaque |
| 94 | 0 | 97 | 187 | 322 | 1.94 | Light yellow, transparent |
| 95 | 0.85 | 95 | 195 | 325 | 2.06 | Partially opaque, crystalline, partial transparent |
| 96 | 17.5(a) | 5 | 7 | 9 | 1.47 | White, crystalline, opaque |
| | 7.1;7.7 | 7 | 8 | 10 | 1.25 | |
| 97 | 4.6 | 116 | 218 | 356 | 1.88 | Light yellow, transparent |
| 98 | 47.7 | — | — | — | — | White, crystalline (monomer), opaque |
| 99 | 65.3 | — | — | — | — | White, crystalline (monomer), opaque |
| 100 | 79.6 | — | — | — | — | White, crystalline (monomer), opaque |
| 101 | 1.4 | 116 | 214 | 340 | 1.84 | Yellow, transparent |
| 102 | 1.9 | 80 | 150 | 235 | 1.87 | Orange, crystalline, opaque |
| 103 | 5.4[i] | 164 | 377 | 657 | 2.30 | Hard, colorless |
| | 2.5;1.9[j] | 307 | 527 | 808 | 1.72 | |
| 104 | 43.3 | 30 | 35 | 41 | 1.17 | Hard, crystalline, opaque |
| 105 | 8.6;9.6 | 219 | 343 | 504 | 1.57 | Hard, crystalline, opaque |
| 106 | 100 | — | — | — | — | All crystalline monomer |
| 107 | 5.0 | 14 | 26 | 35 | 1.88 | White, crystalline, opaque, |
| | film[k] | 14 | 26 | 35 | 1.82 | Some transparency at edges |
| 108 | 20.2[l] | greater than 1,000,000 | | | | White, crystalline opaque |
| 109 | 32.2[m] | greater than 1,000,000 | | | | White, crystalline opaque |

[i]Sample heated at 140°C., then 5 minutes in 60°C. vacuum oven to remove solvent
[j]Sample heated overnight in 60°C. vacuum oven to remove solvent.
[k]Transparent, very stiff and brittle.
[l]Tunc obtains 17.1 percent, very high molecular weight.
[m]Tunc obtains 28.0 percent, very high molecular weight.

Compositions having n equal to an integer between 450 and 10,000 have a good balance between strength and melt processability and are preferred. If a monomer is selected as a plasticizer a unique composition may be obtained by adding monomer that is stereochemically different from that used to obtain the polylactide in the composition. Similarly, addition of oligomer stereochemically different from that which may be obtained during polymerization of the polymer gives a unique product. As tought herein the products are colorless in the absence of coloring agents. Color bodies can be excluded by performing the polymerization in an inert atmosphere and at reaction temperatures preferably at 140 C. or below and by appropriate choice of plasticizer in the composition as described above. During melt processing, a sufficient amount of plasticizer is intimately mixed to prevent discoloration and degradation of molecular weight. Various combinations of the above treatments can be employed to obtain the optimum characteristics as those skilled in the art will appreciate, once knowing the teachings of the invention.

As can be noted in the aforementioned copending application "Pliable Biodegradable Packaging Thermoplastics from Lactides" filed herewith, a higher amount of plasticizer can have significant effect. In the present application, lower amounts of plasticizer are preferred to impart stiffness. Plasticizer present in an amount of between about 0.1 and about 10 weight percent is preferred. The plasticizer can remove molding strains, lubricate, maintain a lower processing temperature, maintain a lower melt viscosity, preserve transparency during melt forming, and regulate degradation time. The composition contains plasticizer in an amount that depends on polymerization conditions or on the amount added after polymerization. The additional material used as plasticizer may be selected from the group: lactic acid, D-lactide, L-lactide, meso D,L-lactide, racemic D,L-lactide, and mixtures thereof. Oligomers of lactide or lactic acid, or oligomeric derivatives of lactic acid, may also be added. Unique compositions may be obtained by addition of monomer different from those selected for the polymers in the composition or oligomers different from those obtained during the polymerization.

Contemplated equivalents of the compositions of the invention are those that contain minor amounts of other materials. The compositions produced in accordance with the present invention can be modified, if desired, by the addition of a cross-linking agent, nucleating agent, other plasticizers, a coloring agent, a filler and the like. Further treatments such as biaxial orientation and heat treatment provide for a useful film that is a replacement for polystyrene.

After treatment there is obtained a biaxially oriented and annealed environmentally decomposable polylactide film or sheet suitable for use as a substitute for biaxially oriented crystal polystyrene film or sheet comprising, a film or sheet of a copolymer of the formula I, where n is between about 450 and about 10,000 prepared from about 85 and 95 weight percent D-lactide or L-lactide and between about 5 and about 15 weight percent D,L-lactide, said film having intimately dispersed therein the residue of a modifier selected from the group consisting of lactic acid, D-lactide, L-lactide, D,L-lactides, oligomers of said acid and said lactides, and mixtures thereof, said oriented and annealed film having a tensile strength in excess of 7,500 a tangent modulus in excess of 350,000, a Tg below about 60 C. and the capacity of being dimensionally heat stable at temperatures of at least 70 C.

The compositions herein can be processed by melt fabrication into useful articles of manufacture having a self supporting structure such as disposable containers, eating utensils, trays, plates, drinking cups, single serving trays, syringes, medical trays, packaging films and the like. The compositions are useful in that they can have the characteristics of the usual plastics (eg. polystyrene) and therefore substitute for them yet degrade in the environment. The amount of plasticizer serves not only as a processing aid, but also governs the initial physical properties. In addition, the amount of plasticizer governs the environmental degradation rate. The compositions are especially useful for articles having only a one time use or a short life span in use before disposal.

Those skilled in the art will now recognize that there are contemplated equivalents for minor amounts of the polymerized lactide and monomeric lactide. These include glycolide, caprolactone, valerolactone, and other cyclic esters as monomers, and the same and/or open chain aliphatic esters as plasticizers.

While the invention has been described above with reference to various specific examples and embodiments, it will be understood that the invention is not limited to such illustrated examples and embodiments and may be variously practiced within the scope of the claims hereinafter made.

I claim:

1. An environmentally decomposable polymeric composition suitable for use as a substitute for cryseal polystyrene comprising a poly(lactic acid), where repeating units of both L- and D- enantiomers are present with a ratio of L- enantiomers to D- enantiomers of less than about 97.5/2.5 and a preponderance of either enantiomer, having intimately dispersed therein between about 1.37 and about 10 weight percent of a plasticizer selected from the group consisting of lactic acid, D-lactide, L-lactide, meso D,L-lactide, racemic D,L-lactide, oligomers of lactic aid, oligomers of lactide, and mixtures thereof in heterogeneous domain sizes of less than one micron; wherein the unoriented composition has a tensile strength of at least about 5,000 psi, a tangent modulus of at least about 200,000 psi, and is colorless and transparent, and wherein said oligomers of lactide and oligomers of lactic acid have number average molecular weights below about 5,400; and wherein the poly(lactic acid) is defined by the formula:

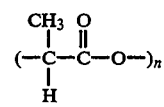

where n is arm integer between about 450 and about 10,000.

2. The composition of claim 1, wherein the plasticizer comprises:
   a. a first plasticizer selected from the group consisting of oligomers of lactic acid, oligomers of lactide, and mixtures thereof, wherein the oligomers of lactic acid and oligomers of lactide have a number average molecular weight below about 5,400; and
   b. a second plasticizer selected from the group consisting of lactic acid, D-lactide, L-lactide, meso D,L-lactide, racemic D,L-lactide, and mixtures thereof.

3. The composition of claim 1, wherein the composition is form stable above about 70 C.

4. The composition of claim 1, comprising a nucleating agent selected from the group consisting of lactate salts, benzoate salts, poly(L-lactide), poly(D-lactide), and mixtures thereof.

5. The composition of claim 1, comprising additional plasticizer dispersed within the composition.

6. The composition of claim 1, comprising a plasticizer selected from the group consisting of lactic acid, D-lactide, L-lactide, meso D,L-lactide, racemic D,L-lactide, and mixtures thereof.

7. The composition of claim 1, comprising a plasticizer selected from the group consisting of oligomers of lactic acid, oligomers of lactide, and mixtures thereof, having a number average molecular weight below about 5,400.

8. The composition of claim 7, wherein the oligomers of lactic acid, and the oligomers of lactide have a number average molecular weight below about 720.

9. The composition of claim 1, wherein the plasticizer is selected from the group consisting of one or more derivatives of an oligomer of lactic acid, defined by the formula:

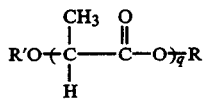

where R=H, alkyl, aryl, alkylaryl or acetyl, and R is saturated,
where R'=H, alkyl, aryl, alkylaryl or acetyl, and R' is saturated,
where R and R' cannot both be H,
and where q is an integer: $2 \leq q \leq 75$.

10. The composition of claim 1, wherein the plasticizer comprises:
a. a first plasticizer selected from the group consisting of oligomers of lactic acid, oligomers of lactide, and mixtures thereof, defined by the formula:

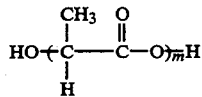

and where m is an integer: $2 \leq m \leq 75$; and
b. a second plasticizer selected from the group consisting of lactic acid, D-lactide, L-lactide, meso D,L-lactide, racemic D,L-lactide, and mixtures thereof.

11. The composition of claim 1, wherein the plasticizer comprises:
a. a first plasticizer selected from the group consisting of one or more derivatives of an oligomer of lactic acid defined by the formula:

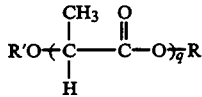

where R=H, alkyl, aryl, alkylaryl or acetyl, and R is saturated,
where R'=H, alkyl, aryl, alkylaryl or acetyl, and R' is saturated,
where R and R' cannot both be H,
and where q is an integer: $2 \leq q \leq 75$; and
b. a second plasticizer selected from the group consisting of lactic acid, D-lactide, L-lactide, meso D,L-lactide, racemic D, L- lactide, and mixtures thereof.

12. The composition of claim 11, comprising: a third plasticizer selected from the group consisting of oligomers of lactic acid, oligomers of lactide, and mixtures thereof, wherein the oligomers of lactic acid and oligomers of lactide have a number average molecular weight below about 5,400.

13. The composition of claim 1, wherein the plasticizer is present in an amount above about 5 weight percent.

14. The composition of claim 1, wherein the polymer is derived from monomer selected from the group consisting of L-lactide, D-lactide, meso D,L-lactide, racemic D,L-lactide, and mixtures thereof; and wherein at least part of the plasticizer is selected from the group of lactides consisting of D-lactide, L-lactide, meso D,L-lactide, racemic D,L-lactide and mixtures thereof, and at least one of the lactides is stereochemically different from the monomer used to prepare the polymer.

15. A process for making an environmentally decomposable polymeric composition suitable for use as a substitute for crystal polystyrene comprising:
(a) providing a first poly(lactic acid) having repeating units of both D- and L- enantiomers and having a preponderance of either enantiomer, said first poly(lactic acid) having a number average molecular weight above about 32,000;
(b) providing a second poly(lactic acid) selected from the group consisting of poly(D-lactic acid) or a poly(L-lactic acid), wherein the weight percent ratio of the first poly(lactic acid) to the second poly(lactic acid) is between about 1/99 and 99/1, said second poly(lactic acid) having a number average molecular weight above about 32,000;
(c) incorporating and blending with the first and second poly(lactic acid) between about 1.37 and about 10 weight percent of plasticizer selected from the group consisting of lactic acid, D-lactide, L-lactide, meso D,L-lactide, racemic D,L-lactide, oligomers of lactic acid, oligomers of lactide, and mixtures thereof, wherein the plasticizer is intimately dispersed within the poly(lactic acids) in heterogeneous domain sizes of less than one micron, said oligomers of lactic acid and oligomers of lactide having a number average molecular weight below about 5,400; and
(d) a physical mixture is obtained wherein the unoriented composition is colorless and transparent and has a tensile strength of at least 5,000 psi and a tangent modulus of at least 200,000 psi.

16. The process of claim 15, wherein the incorporated plasticizer is selected from the group consisting of one or more derivatives of an oligomer of lactic acid, defined by the formula:

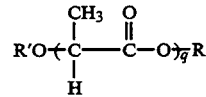

where R=H, alkyl, aryl, alkylaryl or acetyl, and R is saturated,
where R'=H, alkyl, aryl, alkylaryl or acetyl, and R' is saturated,
where R and R' cannot both be H,
and where q is an integer: $2 \leq q \leq 75$.

17. The process of claim 15, wherein the step of incorporating plasticizer comprises:
a. incorporating a first plasticizer selected from the group consisting of one or more derivatives of an oligomer of lactic acid defined by the formula:

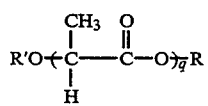

where R=H, alkyl, aryl, alkylaryl or acetyl, and R is saturated, where R'=H, alkyl, aryl, alkylaryl or acetyl, and R' is saturated, where R and R' cannot both be H, and where q is an integer: $2 \leq q \leq 75$; and b. incorporating a second plasticizer selected from the group consisting of lactic acid, D-lactide, L-lactide, meso D,L-lactide, racemic D,L-lactide, and mixtures thereof.

18. The process of claim 15, wherein the ratio of the first poly(lactic acid) to the second poly(lactic acid) is between about 98/2 and about 75/25.

* * * * *

UNITED STATES PATENT AND TRADEMARK OFFICE
CERTIFICATE OF CORRECTION

PATENT NO. : 5,424,346
DATED : June 13, 1995
INVENTOR(S) : Sinclair

It is certified that error appears in the above-identified patent and that said Letters Patent is hereby corrected as shown below:

Claim 1, line 22, delete "cryseal" and insert --crystal-- therefor.

Claim 1, line 47, delete "arm" and insert --an-- therefor.

Claim 11, line 64, delete "D, L- lactide" and insert --D,L-lactide-- therefor.

Signed and Sealed this

Seventh Day of April, 1998

Attest:

BRUCE LEHMAN

*Attesting Officer*  *Commissioner of Patents and Trademarks*